United States Patent [19]
Nayler et al.

[11] 3,959,267
[45] May 25, 1976

[54] 3-(2'-TETRAHYDROPYRANYLMETHYL)-7-(2-THIENYLACETAMIDO)-3-CEPHEM-4-CARBOXYLIC ACID AND NON-TOXIC SALTS THEREOF

[75] Inventors: John Herbert Charles Nayler, Dorking; Michael John Pearson, Roffey; Robert Southgate, Barns Green, all of England

[73] Assignee: Beecham Group Limited, England

[22] Filed: Aug. 30, 1974

[21] Appl. No.: 501,961

Related U.S. Application Data

[62] Division of Ser. No. 303,959, Nov. 6, 1972, abandoned.

[30] Foreign Application Priority Data

Jan. 3, 1972 United Kingdom............... 142/72
Apr. 21, 1972 United Kingdom............... 18694/72
Sept. 9, 1972 United Kingdom............... 41972/72

[52] U.S. Cl.................. 260/243 C; 260/239.1; 260/239 A; 260/345.7; 260/345.8; 424/246
[51] Int. Cl.²........................................ C07D 501/56
[58] Field of Search............................... 260/243 C

[56] References Cited
UNITED STATES PATENTS
3,278,531   10/1966   Cox et al..................... 260/243 C FOREIGN PATENTS OR APPLICATIONS
2,132,883   1/1972   Germany OTHER PUBLICATIONS
Cox et al., Chemical Abstracts, vol. 63, 13246d (1965).

*Primary Examiner*—Alton D. Rollins
*Assistant Examiner*—Diana G. Rivers

[57] ABSTRACT

This invention relates to novel substituted ceph-3-ems some of which are of value as intermediates in the synthesis of antimicrobially active cephalosporin analogues whilst others are useful as antimicrobial agents in their own right. The invention is described in Part D of this specification. Parts A, B, C and E relate to starting materials and processes necessary for the preparation of the novel cephems.

2 Claims, No Drawings

3-(2'-TETRAHYDROPYRANYLMETHYL)-7-(2-THIENYLACETAMIDO)-3-CEPHEM-4-CARBOXYLIC ACID AND NON-TOXIC SALTS THEREOF

This application is a division of application Ser. No. 303,959, filed Nov. 6, 1972, now abandoned.

PART A

Elsewhere we have already described a process for the preparation of substituted azetidin-2-ones of formula (I)

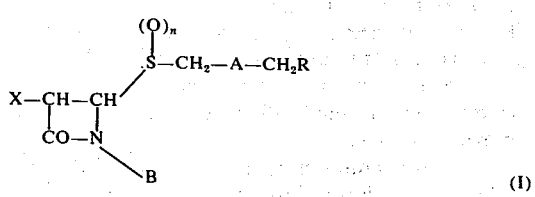

(I)

wherein $n$ represents 0 or 1, X represents an amimo group or a substituted amino group R represents hydrogen or an organic radical; A represents a carbonyl group

or a ketal group

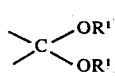

wherein $R^1$ represents $C_1$–$C_3$ alkyl group; and B represents (i) hydrogen, (ii) a group of formula (II)

(II)

wherein $R^2$ represents an esterified carboxylic acid group, (iii) a group of formula (III) or (IIIA)

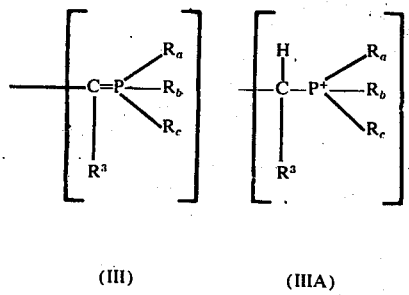

(III)   (IIIA)

wherein $R^3$ is an esterified carboxylic acid group and $R_a$, $R_b$ and $R_c$ are each lower alkyl, aryl or aralkyl groups, any of which may be substituted, or (iv) a group of formula (IIIB):

(IIIB)

wherein $R^3$ is an esterified carboxylic acid group and $R_a^1$ and $R_b^1$ are substituted or unsubstituted alkoxy or aralkoxy groups; which process comprises (i) (when a compound of formula (I) wherein A is a carbonyl group is to be prepared) reacting a compound of formula (IV):

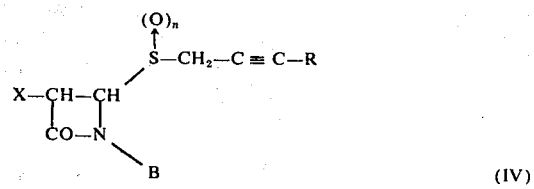

(IV)

wherein $n$, X B and R are as defined with respect to formula (I) with a primary or secondary amine and, if the resultant enamine intermediate does not hydrolyse spontaneously, subsequently subjecting the resultant enamine intermediate to acid hydrolysis to form the desired compound of formula (I) or (ii) (again when a compound of formula (I) wherein A is a carbonyl group is to be prepared) reacting a compound of formula (IV) above with water in the presence of a source of mercuric ions as catalyst or (iii) (when a compound of formula (I) wherein A is a ketal group is to be prepared), reacting a compound of formula (IV) above with a lower alkanol in the presence of a source of mercuric ions as catalyst.

The reaction of the acetylenic compound (IV) with the primary or secondary amine under step (i) above may produce one of two possible enamine intermediates or a mixture of both i.e.

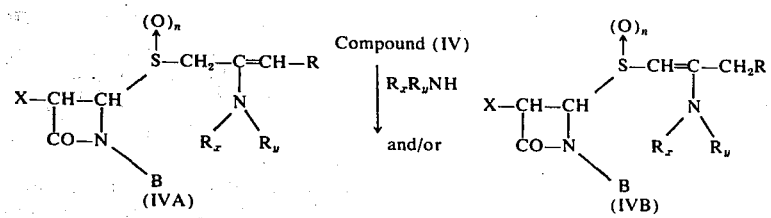

(IVA)        (IVB)

In addition, it is believed that the formation of the enamines from acetylenic compounds (IV) may (at least in some cases) proceed through an intermediate allene.

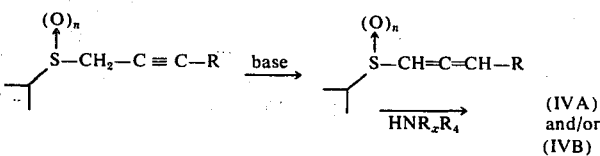

(IVA) and/or (IVB)

The process described in the preceding paragraph produces substituted azetidin-2-ones of formula (I).

In formula (I) the group X has been defined as an amino or substituted amino group. The term "substituted amino group" includes both mono- and di- substituted amino groups.

Compounds of formula (I) are made from compounds of formula (IV) as starting materials. The group X in compounds (IV) should survive the reaction conditions to end up as the group X in compounds (I). Since free amino groups or protonated amino groups tend to be somewhat reactive, it is not always desirable to carry out the reaction using compounds (IV) wherein X is either of these groups. Preferably the starting material (IV) is one wherein the group X is a substituted amino group. The identity of the substituents is not critical, but they should naturally be such that the entire substituted amino group X is stable under the particular reaction conditions chosen. If the particular substituted amino group chosen is one which can be converted to a free amino group without disruption of the β-lactam ring of compounds (I), then it may be preferable to prepare compounds (I) wherein X is a free amino group by starting from compound (IV) wherein X is a substituted amino group, and subsequently removing the substituents. Examples of substituted amino groups X which can be present in the starting materials (IV) and which, after the reaction to produce compounds (I) can be converted to free amino groups include triphenylmethylamino (the triphenylmethyl group being removable by acid hydrolysis or catalytic hydrogenation); t-butoxy-carbonylamino (removable by treatment with anhydrous acid); trichlorethoxycarbonylamino (removable by reduction with zinc and acetic acid) acylamino groups, e.g. phenylacetylamino or phenoxyacetylamino (removable, if desired, either enzymically or by known chemical procedures.).

Referring again to the products of the process described above, i.e. the substituted azetidin-2-ones (I), it will be noted that the group B is hydrogen or one of the groups (II), (III), (IIIA), or (IIIB). When B is a group of formula (II), (III), (IIIA), or (IIIB), the groups $R^2$ and $R^3$ have been defined as esterified carboxylic acid groups. Again, this esterified carboxylic acid group takes no part in the reaction described above, and its identity is in this respect not critical. However, the most versatile compounds (I) are obtained when R2 and $R^3$ are esterified carboxylic acid groups which can be readily converted to free carboxylic acid groups without damage to the remainder of the molecule. Examples of such esters include the t-butyl and p-methoxybenzyl esters (both removable with a strong anhydrous acid such as trifluoroacetic acid). However, on occasions other, perhaps less readily removable esters may be employed e.g.; — lower alkyl esters or thioesters (e.g. methyl, ethyl or propyl esters or thioesters); aralkyl esters or thioesters (e.g. benzyl, substituted benzyl or benzhydryl esters or thioesters); aryl esters or thioesters (e.g. phenyl or substituted phenyl esters or thioesters); acyloxyalkyl esters (e.g. acetoxymethyl or pivaloyloxymethyl esters).

The group R in the starting materials of formula (IV) (and thus also in the end products of formula (I) has been widely defined as hydrogen or an organic group. We find that by choosing the reaction conditions and starting materials carefully, the reaction described above can be carried out with a wide range of organic groups R present in the starting materials. More will be said about the relationship between the group R and the reaction conditions later, but for the present it will be sufficient to state that, in general, R may be hydrogen, substituted or unsubstituted alkyl, substituted or unsubstituted aralkyl; substituted or unsubstituted aryl or a heterocyclic group which may carry ring substituents. In particular, R may be an unsubstituted $C_1$ to $C_6$ alkyl or cycloalkyl group; a phenyl group; a phenylalkyl group wherein the alkyl portion contains from 1 to 4 carbon atoms, an alkoxyalkyl group having from 1 to 4 carbon atoms in each alkyl portion or a monocyclic heterocyclic group.

In the preceding paragraphs, reference has been made to the relationship between the reaction conditions and the identity of various groups on the starting material (IV). Before discussing this relationship in some depth it should be noted that suitable "sources of mercuric ions" useful in steps (ii) and (iii) of the process described above include mercuric sulphate in dilute sulphuric acid; mercuric chloride in piperidine, morpholine or pyrrolidine, mercuric acetate, mercury acetamide, mercury p-toluene sulphonamide and a mercury-impregnated polystyrene resin in aqueous acetic acid. With water as the reactant ie. in step (ii) of the process described above, it is convenient to include in the reaction mixture an organic solvent for the starting material (IV) such as a lower alkanol, acetic acid, acetone, dioxan, ethyl acetate, dimethyl formamide, dimethyl sulphoxide or tetrahydrofuran. In general, addition of water to the triple bond occurs more readily than that of an alkanol. Hence when both water and alkanol are present the ketone

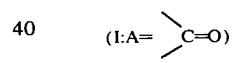

is usually the main product although some ketal

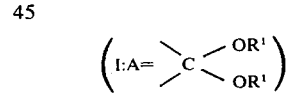

may also be formed, particularly if the quantity of alkanol present greatly exceeds that of water.

When it is desired to obtain the ketal as the major product the quantity of water present should be kept to a minimum, and it is convenient to employ the alkanol as solvent as well as reactant. Addition of the alkanol to the triple bond of compound (IV) may be catalysed by the previously mentioned mercury compounds. Alternatively, a specific catalyst which minimises the risk of hydrolysis may be formed by heating together momentarily red mercuric oxide, ether-boron trifluoride complex, trichloroacetic acid, and the appropriate lower alkanol.

Addition of either water or lower alkanol to the triple bond may be accomplished at temperatures between 0°C and 100°C but proceeds faster at the higher temperatures.

It will be seen that the process described above defines two methods for the preparation of compounds of formula (I) wherein A is the carbonyl group. In the first, the acetylenic sulphide or sulphoxide (IV) is reacted with a primary or secondary amine to form an enamine compound which then hydrolyses spontaneously to form the desired product or is subjected to acid hydrolysis to form the desired product. Sometimes hydrolysis is effected merely by subjecting the enamine compound to silica gel chromatography. In the second, the acetylenic sulphide or sulphoxide (IV) is hydrated with water in the presence of mercuric ions.

When the sulphide or sulphoxide (IV) is reacted with a primary or secondary amine, we find that the reaction proceeds much faster with sulphoxide (IV n=1) than with sulphide (IV n=0). Preferred amines include cyclic secondary amines such as piperidine, morpholine and pyrrolidine, but other secondary amines as dimethylamine, diethylamine, dibenzylamine and primary amines such as ethylamine, n-butylamine, benzylamine, cyclohexylamine and t-butylamine may be used on occasions, especially with sulphoxides.

When the sulphides or sulphoxide (IV) is reacted with water in the presence of the mercuric catalyst it has already been stated that the identity of the groups X, B and R in the starting materials influences the choice of catalyst.

When the catalyst is mercuric sulphate/acid (in methanol, for example) the presence of acid makes it essential that the groups X and R in compounds (IV) should be acid stable. The mercury impregnated polystyrene resin aqueous acid appears to be useful in much the same circumstances as $HgSO_4/H^+$, although it is less active.

When mercuric acetate, mercury acetamide, or mercury p-toluene sulphonamide is the catalyst, the groups X and R on starting material (IV) need not be acid stable, but these catalysts appear to be effective only where R = H.

The catalyst formed by heating together momentarily red mercuric oxide, ether-boron trifluoride complex, trichloroacetic acid and the appropriate lower alkanol appears to be effective only with compounds (IV) where X is acid stable and R = H.

If desired mercuric salts may also be included in the procedure which comprises treating the acetylene derivative (IV) with a primary or secondary amine to give an enamine, which in turn undergoes hydrolysis to the ketone (I A=CO). Such a procedure is typified by the use of mercuric chloride in piperidine. In certain cases, particularly when R = H and n=0, reactions which only occur on heating when piperidine is used alone takes place at room temperature when mercuric chloride is included. In other cases, particularly when R is an organic radical, use of a mercury salt in combination with a primary or secondary amine appears to offer little or no advantage over the use of the amine alone.

To summarise, the most generally useful procedure for converting the acetylene derivative (IV) into the corresponding ketone (I, A=CO) is reaction with a primary or secondary amine, either alone or in the presence of a mercury salt, followed by very mild acid hydrolysis of the intermediate enamine. This procedure is particularly advantageous when X is an acidlabile group such as tritylamine. Addition to the triple bond occurs faster when $n=1$ than when $n=0$ and in certain instances, as when R is methyl, ethyl or benzyl, only occurs at an appreciable rate when $n=1$.

Direct addition of water to the triple bond in the presence of a mercury compound as catalyst is chiefly useful when R = H and, if acidic conditions are employed, when X is acidstable.

In addition, $HgCl_2$/piperidine is not effective with compounds (IV) where B = H. If in any case it is desired to prepare compounds (I) where n=0 (i.e. the sulphide), and the process described above only allows the preparation of the corresponding compounds where n=1 (i.e. the sulphoxide) then the sulphoxide can be converted to the sulphide by methods known for reducing penicillin or cephalosporin sulphoxides to the parent penicillins and cephalosporins. Such methods are described for example in Belgian Pat. No. 737121.

The starting materials of formula (IV) are obtained in various ways as will become clear from the ensuing discussion:

Compounds of formula (IV) wherein n=0, B=a group of formula (II), X is a substituted amino group and R is defined with reference to formula (I) may be prepared by a process which comprises reacting a penicillanic acid derivative of formula (V):

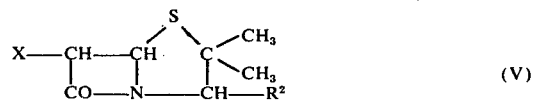
(V)

where X is a substituted amino group and $R^2$ is defined with respect to formula (I) in a substantially anhydrous liquid medium with a strong base which does not cleave the β-lactam ring of the penicillanic acid derivative (V) and a reagent of formula (VI):

wherein R is as defined with reference to formula (I) and Z is a reactive atom or group of effecting the introduction of the group $+CH_2—C ≡ C—R]$ onto the sulphur atom. This reaction generally produces a starting material of formula (IV) wherein n=0, B= group of formula (II) and X and R are as defined with reference to formula (I). However, with some bases and with some of the compounds (VI) rearrangement of the multiple bond may occur, so that the resultant product is actually a mixture of starting materials (IV) and (IVA):

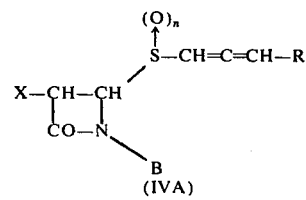
(IVA)

wherein n=0, b= groups of formula (II) and X and R are as defined with reference to formula (I). These two products may be identified spectroscopically and, if desired, can be separated by conventional means such as chromatography. However, it may not be necessary to isolate the isomers, since the mixture may sometimes be employed in the process of this invention.

Suitable strong bases which can be used to cleave the thiazolidine ring of compounds (V) include the alkali metal hydrides, particularly sodium hydride, the alkali metal tertiary alkoxides e.g. potassium t-butoxide and the organo-derivatives of alkali metals such as sodium dimethylsulphoxide. In general, mixtures of compounds (IV) and (IVA) are more commonly obtained with alkali metal tertiary alkoxides than with other bases, but it is as yet impossible to generalise.

The reactive atom or group Z present in the compound (VI) may be a halogen atom, particularly bromine or iodine. The anydrous medium in which the reaction is carried out may be tetrahydrofuran, dimethylformamide, dimethylsulphoxide or a mixture of t-butanol and tetrahydrofuran.

Starting materials of formula (IV) wherein $n=1$, B= a group of formula (II) and X and R are as defined with reference to formula (I) may be obtained by oxidation of the corresponding sulphide compound ($n=0$). Such oxidation may be carried out using the techniques known for converting penicillins into penicillin sulphoxides, e.g. by treatment of the sulphide with $H_2O_2$ or a peracid (particularly m- chloroperbenzoic acid).

Starting materials of formula (IV) wherein $n=0$, B= hydrogen and X and R are as defined in formula (I) can be prepared by treating the corresponding compound where B= a group of formula (II) with a reagent capable of adding oxidatively to a double bond e.g. osmium tetroxide or, preferably, potassium permanganate. This reaction removes the group (II) from the nitrogen atom of the azetidin-2-one ring and gives the desired compound (IV) wherein B=H. [A side rection which may take place is oxidation at the sulphur atom to form a sulphone. This side reaction can be minimised by using mild reaction conditions]. When potassium permanganate is the reagent, the reaction can be carried out in various solvents such as acetone, aqueous acetone, pyridine and aqueous pyridine, at a temperature of from $-20°C$ to $+10°C$.

Starting materials of formula (IV) wherein n=1, B= hydrogen and X and R are as defined with respect to formula (I) may be obtained by oxidation of the corresponding sulphide compound using $H_2O_2$ or a peracid such as m-chloroperbenzoic acid.

Starting materials of formula (IV) wherein $n=0$ B= a group of formula (III), or (IIIA) or (IIIB) and X and R are as defined may be prepared by a process which comprises reacting the corresponding compounds (IV) wherein $n=0$, B= hydrogen and X and R are as defined with reference to formula (I) with an ester of glyoxylic acid, thereby producing a compound of formula (VII):

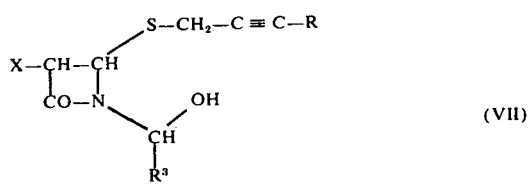

(VII)

wherein X and R are as defined with reference to formula (I) and $R^3$ is an esterified carboxylic acid group reacting the compound (VII) with thionyl chloride to produce a compound of formula (VIIA):

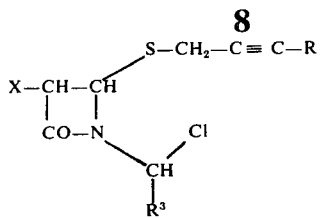

(VIIA)

wherein X, R and $R^3$ are as already defined, and then reacting the compound of formula (VIIA) with a phosphine of formula (IIIC):

(IIIC)

wherein $R_a$, $R_b$ and $R_c$ are as defined with reference to formula (III) or (IIIA) or a phosphine of formula (IIID):

(IIID)

wherein $R_a^1$, $R_b^1$ and $R_c^1$ are substituted or unsubstituted alkoxy or aralkoxy groups.

The first step in the above process, i.e. the reaction with the ester of glyoxylic acid can be effected by refluxing the reaction components in dry benzene with provision for continuously removing water. The second step, i.e. the reaction with thionyl chloride should be carried out in an inert solvent, e.g. dry tetrahydrofuran and/or dioxan in the presence of an acid acceptor such as pyridine, under an inert atmosphere. Thionyl chloride should be added to the reaction mixture in a dropwise fashion. The third step, i.e. the reaction with the phosphine (IIIC) or (IIID) should also be carried out in an inert solvent such as tetrahydrofuran and/or dioxan in the presence of an acid acceptor. Further details of these steps may be found in British Patent Specification No. 1,248,130.

Starting materials of formula (IV) wherein $n=1$, B= a group of formula (III), (IIIA) or (IIIB) and X and R are as defined may be prepared by oxidation of the appropriate compound of formula (VIIA) using, for example $H_2O_2$ or a peracid such as m-chloroperbenzoic acid, and then treating the resultant sulphoxide with the appropriate phosphine compound in the usual way.

PART B

The process described in Part A of this Specification permits the preparation of a class of substituted azetidin-2-ones of formula (I):

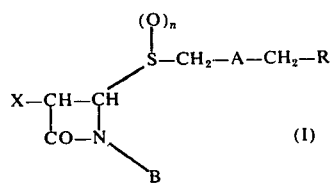

(I)

wherein $n$ represents 0 or 1; X represents an amino or substituted amino group; R represents hydrogen or an organic radical; A represents a carbonyl group

or a ketal group

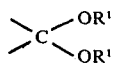

wherein $R^1$ represents a lower alkyl, group; and B represents (i) hydrogen, (ii) a group of formula (II):

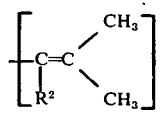
(II)

wherein $R^2$ represents an esterified carboxylic acid group; (iii) a group of formula (III) or (IIIa):

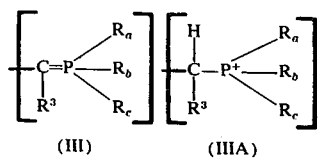

(III)    (IIIA)

wherein $R^3$ is an esterified carboxylic acid group and $R_a$, $R_b$ and $R_c$ are each lower alkyl, aryl or aralkyl groups, any of which may be substituted, or (IV) a group of formula (IIIB):

$$\left[ \begin{array}{c} H \\ -C-P \\ R^3 \end{array} \begin{array}{c} O \\ R_a^1 \\ R_b^1 \end{array} \right]$$
(IIIB)

wherein $R_a^1$ and $R_b^1$ are substituted or unsubstituted alkoxy or aralkoxy groups.

The definitions of the symbols occurring in the above formulae (I), (II), (III), (IIIA) and (IIIB) have been dealt with in some depth in Part A of this specification, and the method for preparing the compounds (I) has also been discussed.

However, although all of the compounds of formula (I) above are useful as intermediates in the synthesis of substituted ceph-3-ems, some are useful at different stages in the synthesis than others. Thus, only compounds of formula (I) wherein X is amino or substituted amino, $n=0$ or 1,

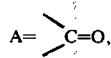

R = an organic group and B = a group of formula (III), (IIIA) or (IIIB) are useful as direct precursors of substituted ceph-3-ems. The remaining compounds of formula (I) are useful for conversion to these direct precursors and are therefore intermediates at an earlier stage in the synthesis as will be apparent from the following typical reaction schemes. Schemes I, II and III below are illustrative only, and it should be understood that the order in which the various steps are carried out may be varied, depending on the identity of the various intermediates.

SCHEME I

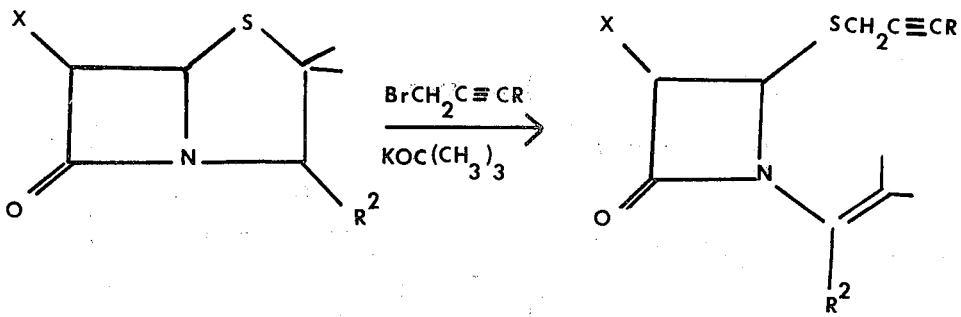

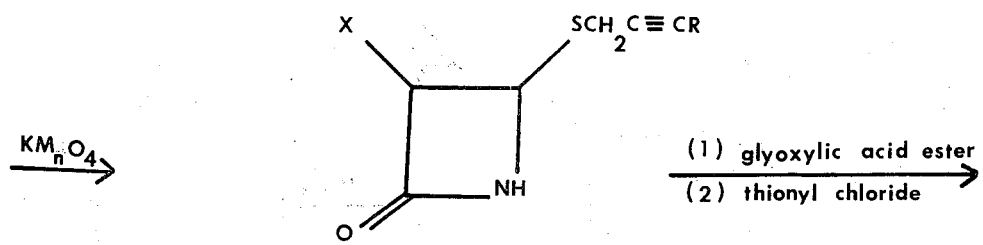

11  12
-continued
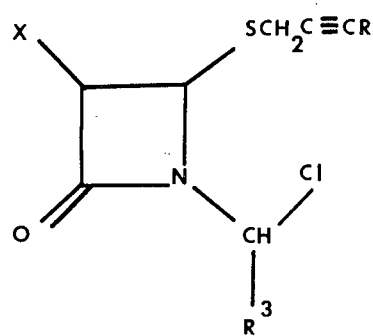 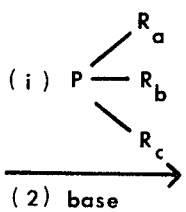 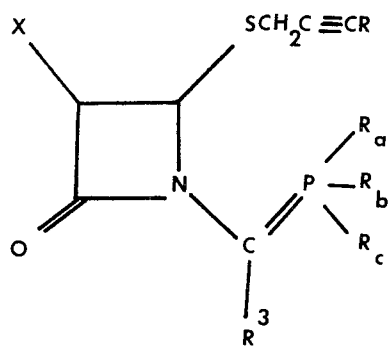
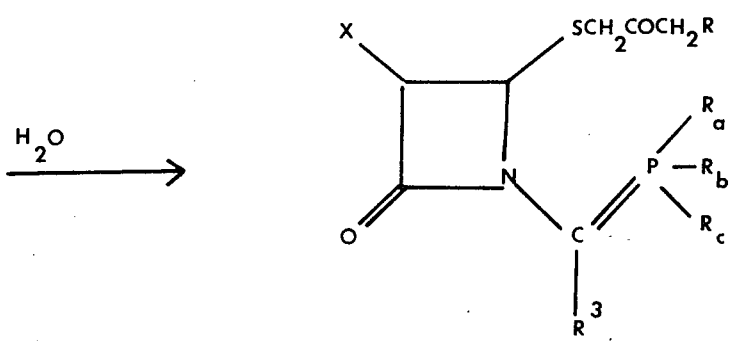
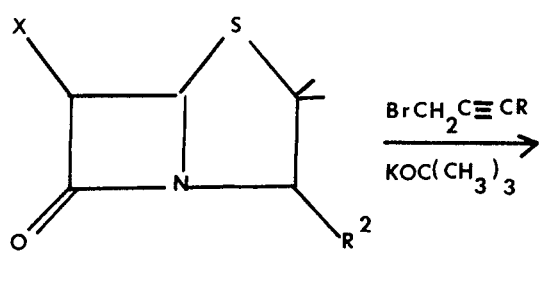 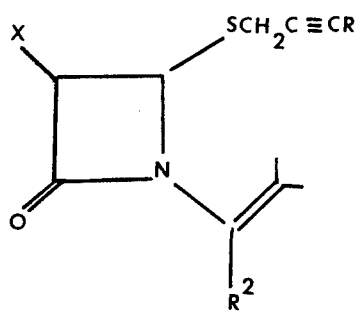
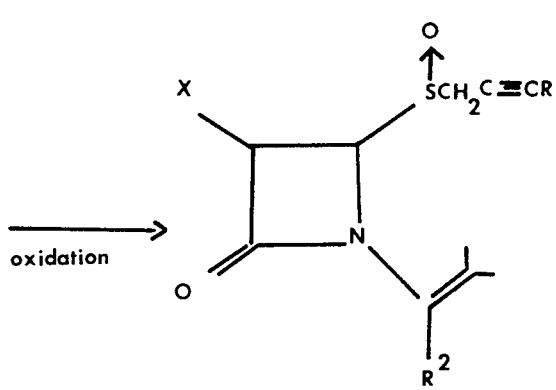 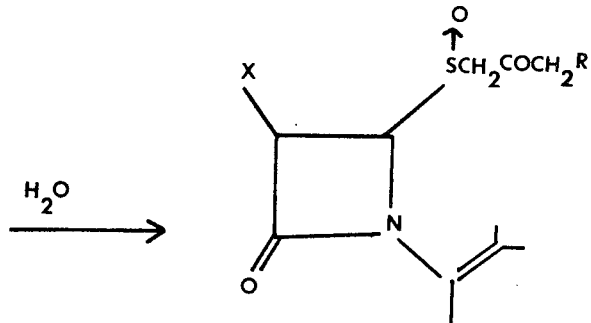
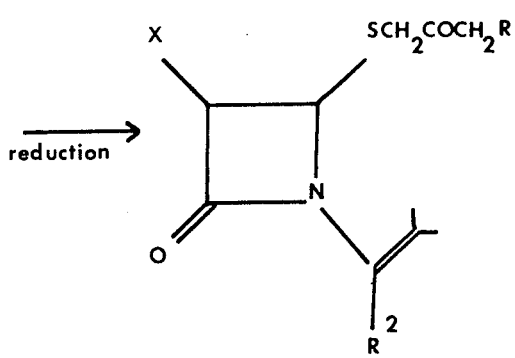  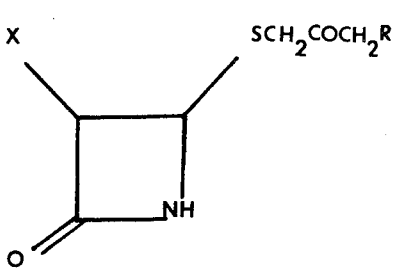

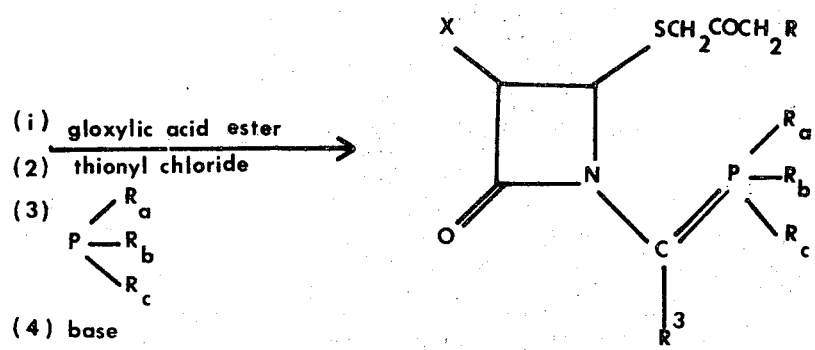
SCHEME II
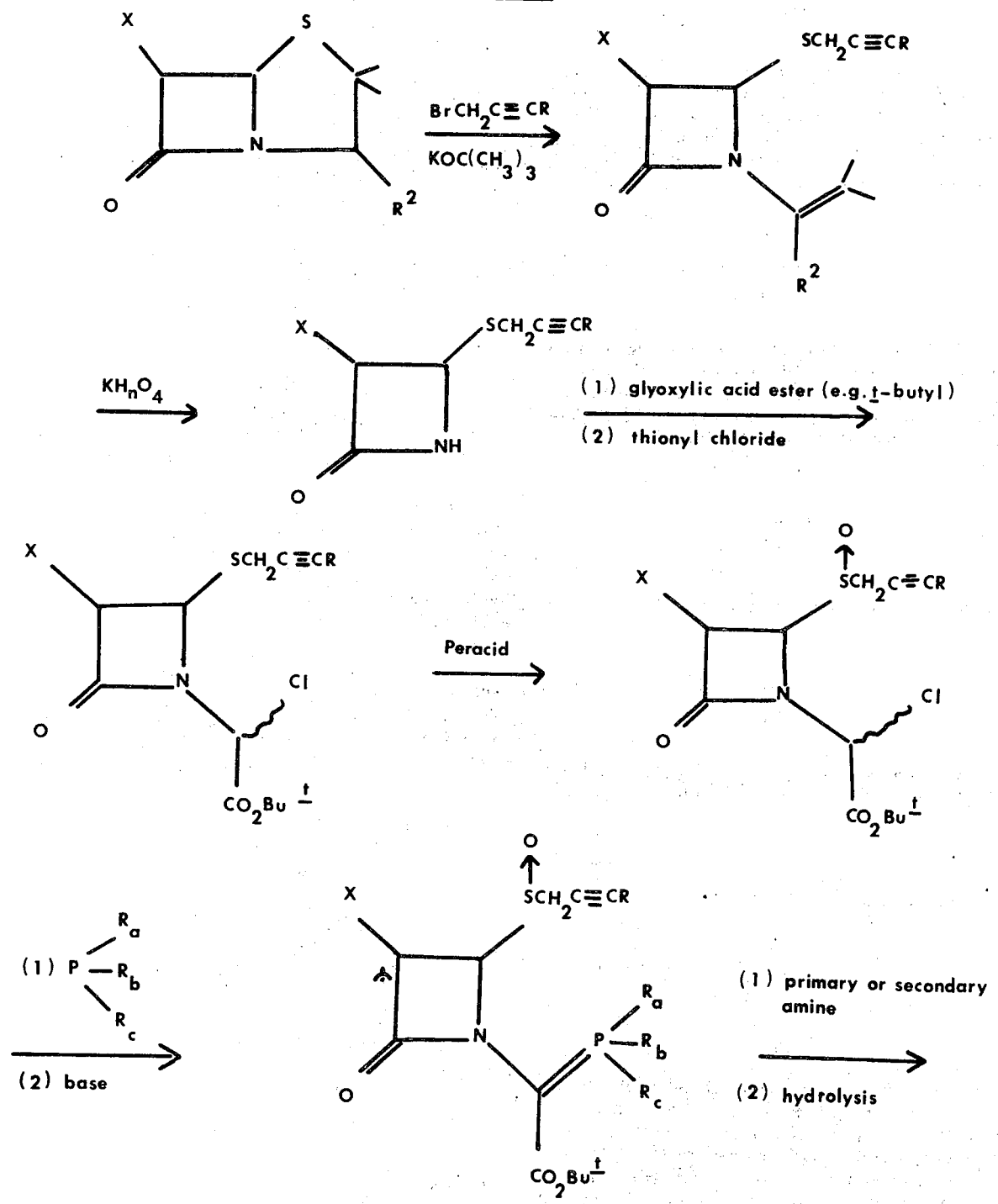

15
-continued

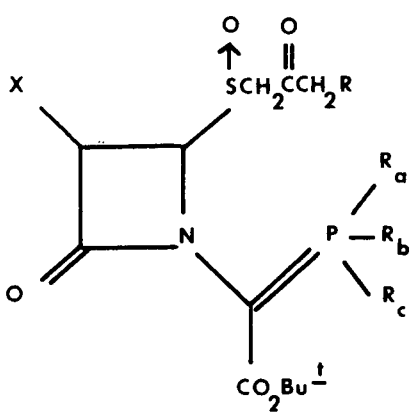

In each of the above schemes, the individual steps have been described generally in Part A of this specification. Each scheme contains a step which has been represented as the reaction of the chloro- intermediate (formed after the addition of thionyl chloride) with the phosphine compound

(here $R_a$, $R_b$ and $R_c$ have the same meaning as in formula (III), (IIIA) and (IIIB)) followed by the addition of a base (the base being necessary to convert any of phosphonium compound to the desired neutral phosphorane). If, instead of the phosphine compound

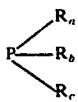

an alternative phosphine compound

had been used ($R_a^1$, $R_b^1$ and $R_c^1$ being alkoxy or aralkoxy groups) the final product would have been one of formula:

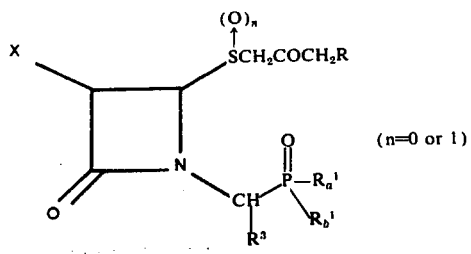

In addition to the steps shown in Schemes I, II and III it would be possible, should one wish to do so, to change the identity of the group X. For example if X was originally a suitable substituted amino group such as trityl it would be possible to remove the trityl group at almost any stage, to produce a free amino group, which could then, if desired, be acylated (e.g. to produce the phenoxyacetylamino group) or converted to a different substituted amino group in some other manner. In general however, we prefer to retain the same group X throughout the reaction scheme.

Both reaction Schemes I, II and III above include a step which corresponds to the process of this invention described in Part A of this specification, namely hydration of the triple bond of the S-substituent. The ketal compound sometimes gives better yields after the oxidative removal of the isopropylidene group, than does the corresponding ketone. Ketals can, of course, be prepared in high yields from the corresponding ketone and can be converted back to the ketone compound by treatment with acid. Thus in such cases, the group X should be acid stable.

Since they are the immediate precursors of the desired ceph-3-ems structures, a preferred class of compounds of this invention have formula (IA) or (IB):

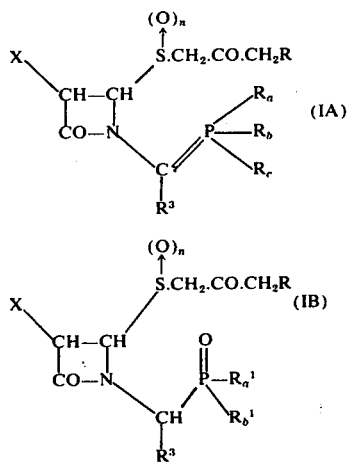

wherein $n=0$ or 1; X is an amino group, a protonated amino group or a substituted amino group; R is hydrogen an organic radical; $R^3$ is an esterified carboxylic acid group; $R_a$, $R_b$ and $R_c$ are each lower alkyl, aryl or aralkyl groups, any of which may be substituted; and $R_a^1$ and $R_b^1$ are each substituted or unsubstituted lower alkoxy or aralkoxy groups. The compounds (IA) and (IB) can exist in several stereoisomeric forms. The preferred configurations is that depicted in formulae (IA¹) and (IB¹) below (N.B.: the stereo- configuration of the sulphoxides (IA¹) and (IB¹) has not been specified since neither isomer is especially preferred).

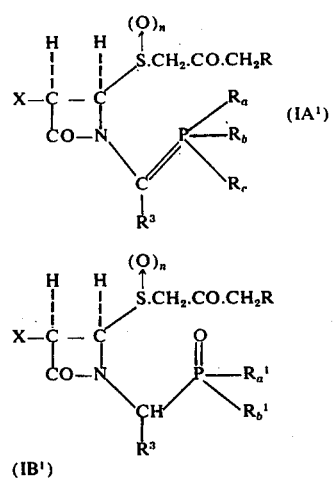

The utility and a further description of the compounds of formula (IA) or (IB) will become apparent from the following Part C of this specification.

PART C

In part B above, it was said that the specific class of substituted azetidin-2-ones having formula (IA) or (IB) above were the immediate precursors of substituted ceph-3-ems. Such precursors are of value in a process for the preparation of substituted ceph-3-ems and ceph-3-em sulphoxides of formula (VIII):

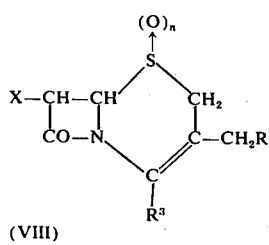

(VIII)

wherein $n = 0$ or 1, X is a substituted amino group $R^3$ is an esterified carboxylic acid group and R is hydrogen or an organic radical which process comprises first preparing a compound of formula (IA) or (IB).

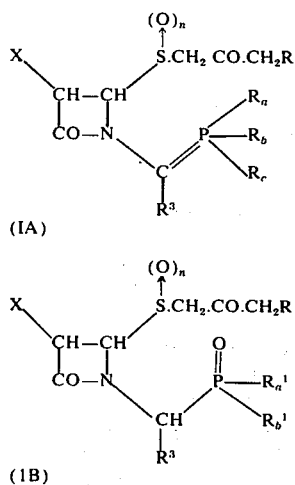

wherein $n$, X, R and $R^3$ are as defined with respect to formula (VIII) above, $R_a$, $R_b$ and $R_c$ are substituted or unsubstituted lower alkyl, aryl or aralkyl groups, $R_a^1$ and $R_b^1$ are substituted or unsubstituted alkoxy or aralkoxy groups; and then heating said compound of formula (IA) or (IB) at a temperature of from 30°C to 150°C in an inert organic solvent thereby producing the desired compound of formula (VIII). Preferably the temperature is from 75°C to 125°C.

Suitable solvents are those which are inert under the reaction conditions and which boil between 30°C and 150°C e.g. dioxan, toluene and benzene. High boiling solvents are difficult to remove after the reaction and are therefore not preferred. For a clean reaction, we prefer to carry the cyclisation out under an inert atmosphere, e.g. $N_2$, although this is not essential. In addition it is preferable to dry the solvent thoroughly to avoid any decomposition of the starting material.

Compounds of formula (IA) or (IB) may be prepared in two ways. In the first method a compound of formula (IX):

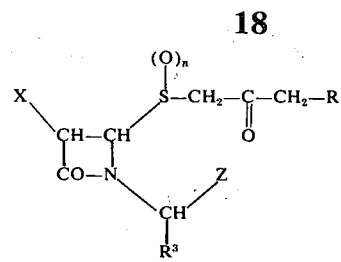

(IX)

wherein $n$, X, R and $R^3$ are as defined with respect to formula (VIII) and Z is a halogen atom, or an organic sulphonyloxy group is reacted (i) with a phosphine compound of the formula (IIIC) if a compound of formula (IA) is to be produced:

wherein $R_a$, $R_b$ and $R_c$ are as defined with respect to formula (IA), and, if necessary, a phosphonium salt compound resulting as an intermediate product is converted to the desired compound of formula (IA) by elimination of the elements of the acid HZ, or (ii) with a compound of formula (IIID) if the compound of formula (IB) is to be produced:

wherein $R_a^1$, $R_b^1$ and $R_c^1$ are substituted or unsubstituted alkoxy or aralkoxy groups.

The reactive group Z in formula (IX) may be a halogen atom, preferably chlorine or bromine, or an organic sulphonyloxy group, e.g. p-toluene sulphonyloxy.

The radicals $R_a$, $R_b$ and $R_c$ in the phosphine compound of formula (IIIC) may be optionally substituted lower alkyl or aryl (preferably phenyl) radicals, and the radicals $R_a^1$, $R_b^1$ and $R_c^1$ in the phosphine compound (IIID) may be optionally substituted lower alkoxy radicals e.g., methoxy or ethoxy, radicals.

If a phosphonium compound is obtained as an intermediate during the preparation of compounds (IA) the elements of the acid HX may be eliminated by treatment with a weak base e.g., pyridine.

In a second method for the preparation of compounds of formula (IA) or (IB), a compound of formula (X):

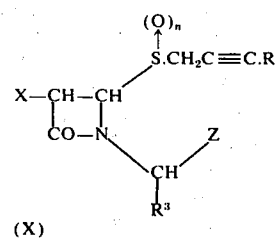

(X)

wherein X, R and $R^3$ are as defined with respect to formula (VIII) and Z is as defined with respect to formula (IX), is reacted with a phosphine compound of formula (IIIC) or (IIID), and, if necessary a phosphonium salt compound resulting as an intermediate product is converted by the elimination of the elements of the acid HZ to a compound of formula (XI) or (XIA) as the case may be:

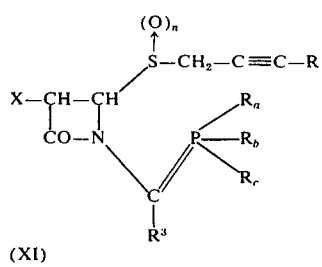

(XI)

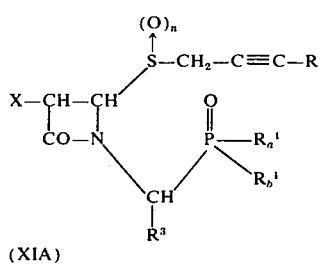

(XIA)

X, R, $R^3$, $R_a$, $R_b$, $R_c$, $R_a{}^1$ and $R_b{}^1$ being as defined above and the compound of formula (XI) or (XIA) is then (i) treated with a primary or secondary amine, and, if the resultant enamine intermediate does not hydrolyse spontaneously, the resultant enamine intermediate is subsequently subjected to acid hydrolysis or (ii) treated with water in the presence of a source of mercuric ions, or (iii) treated with a $C_1$–$C_3$ alkanol in the presence of a source of mercuric ions and an acid. Methods (ii) and (iii) are chiefly useful when R=H.

It will, of course, be recognised that the process described in the preceding paragraph is simply the process described in Part A herein, applied to a compound (XI) or (XIA), and the discussion of the reaction in Part A applies also in the present instance.

In compounds (IA) and (IB) above, the group X is a substituted amino group. The term "substituted amino group" includes both mono- and di-substituted amino groups. After the cyclisation of (IA) or (IB), on heating in inert solvent the group X survives unchanged to end up in the 7-position of the substituted ceph-3-em or ceph-3-em sulphoxide (VIII). Since the known antibacterially active cephalosporins have acylamino groups in the 7-position it may sometimes be desirable that the groups X in compounds (VIII) should be an acylamino group. This can be achieved for example by cyclisation of compounds (IA) or (IB) wherein X is the desired acylamino group, or (where the desired acylamino group either will not survive the cyclisation step or interferes with the efficiency of the cyclisation step) by cyclisation of compound (IA) or (IB) wherein X is a protected amino group thereby forming a compound (VIII) where X is a protected amino group, and thereafter removing the protecting group and acylating the free amino group by any of the methods known for acylating 7-aminocephalosporanic acid.

Examples of non-acylamino substituted amino groups X which may be present in compounds (IA) or (IB) and which usually survive the cyclisation step include triphenylmethylamino, t-butoxycarbonylamino and trichloroethoxycarbonylamino. Acylamino groups which appear to survive the cyclisation step include phenoxyacetylamino, α-(t-butoxycarbonylamino) phenylacetylamino and 2-thienylacetylamino groups, although theoretically there is no reason why almost any acylamino group known in the antibacterially active penicillins and cephalosporins should not be present in compounds (IA) or (IB). If the desired acylamino group contains a reactive group such as $NH_2$, this group may be protected during the course of the reaction.

The group $R^3$ in compounds (IA) and (IB) is an esterified carboxylic acid group. Whilst almost any esterified carboxylic acid group may be employed, we have noticed a tendency for strongly electron-withdrawing esters to reduce the yield of the cyclised product (VII). Thus, in general, strongly-electron withdrawing esters such as the trichloroethyl ester should preferably be avoided. By analogy with the known antibacterially active penicillins and cephalosporins, it is to be expected that compounds of formula (VIII) wherein $R^3$ is an esterified carboxylic acid group are likely to be less active than the corresponding compounds where $R^3$ is free acid group or a salt of a free acid group. Thus it is preferred that the group $R^3$ in compounds (IA) or (IB) (which of course survive the cyclisation stage unchanged) should be one which is easily converted later to a free carboxylic acid group. Examples of such esters include the t-butyl and p-methoxybenzyl esters (both removable with a strong anhydrous acid such as trifluoroacetic acid). However, on occasions other, perhaps less readily removable esters may be employed e.g.; lower alkyl esters or thioesters (e.g. methyl, ethyl or propyl esters or thioesters); aralkyl esters or thioesters (e.g. benzyl, substituted benzyl or benzhydryl esters or thioesters); aryl esters or thioesters (e.g. phenyl or substituted phenyl esters or thioesters); acyloxyakyl esters (e.g. acetoxymethyl or pivaloyloxymethyl esters).

The group R in compounds (IA) and (IB) above is hydrogen or an organic group. Since the group $CH_2R$ ends up in the 3-position of compounds (VIII), and since the identity of groups of the 3-position of the known cephalosporins are known to have an effect on the antibacterial activity of the cephalosporins clearly the process of this invention is of great importance and versatility. It enables $CH_2R$ wherein R is hydrogen or almost any organic group to be introduced at the 3-position of the ceph-3-em ring where most of the previously available methods for modifying the groups at this position only allowed the substitution of the 3-acetoxy group of natural cephalosporins by hydrogen or nucleophilic groups. Among the organic groups R which may be present in compounds (IA) or (IB) (and therefore in compound (VIII)) are alkyl groups and substituted alkyl, e.g. methyl, ethyl, n and iso-propyl, n-, sec- and tert-butyl, cyclopentyl, cyclohexyl; alkoxyalkyl groups, e.g. methoxyethyl, ethoxyethyl; acyloxy groups, e.g. acetoxy, aryl groups e.g. phenyl, naphthyl; substituted phenyl and naphthyl groups, e.g. those when the substituents are hydroxy, alkoxy, aralkoxy, carboxylic acid, salt, ester or amide derivatives of carboxylic acid groups, nitro, amino substituted amino, halogen or lower alkyl groups; aralkyl groups, e.g. benzyl, substituted benzyl, phenylethyl, substituted phenylethyl; heterocyclic groups such as tetrahydropyranyl, tetrahydropyranyloxymethyl and 2-, 3- or 4- pyridyl.

Since the cyclisation process outlined above is one step in a synthetic sequence designed to produce antibacterially active ceph-3-ems, the preferred configuration of the starting materials (IA) and (IB) above, is that found in the naturally occurring active cephalosporins, namely that shown in formulae (IA¹) and (IB¹) above.

Cephem sulphoxides of formula (VIII) may be reduced to cephems themselves by any of the conventional known methods e.g. those described in British Pat. No. 1,280,693. One such method which we have found particularly useful is treatment with triphenylphosphine and acetylchloride.

It will be clear from the above discussion that the cyclisation process outlined allows the formation of a large number of substituted ceph-3-ems. Many of the compounds which can be formed by this process are esters of known cephalosporins and cephalosporin sulphoxides but some of the compounds (VIII) are new compounds in jtheir own right, not previously accessible by the known routes. The ensuing Part D of this specification deals with some of these new structures.

PART D

In Part C of this specification we described a process for the preparation of some substituted ceph-3-ems and ceph-3-em sulphoxides which can be reduced to ceph-3-ems. Certain of these ceph-3-ems are new compounds in their own right, some of them having antimicrobial activity and the remainder being useful as intermediates for conversion to antimicrobially active compounds.

Thus, according to the present invention there is provided a class of substituted ceph-3-ems of formula (VIIIA)

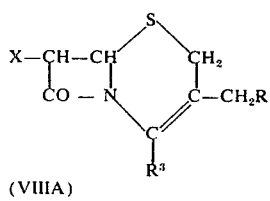

(VIIIA)

wherein X is a substituted amino group R³ is a carboxylic acid group or a salt or ester of a carboxylic acid group and R is a $C_2$ to $C_{10}$ alkyl or substituted alkyl group, a phenyl or halo- substituted phenyl group, a phenylalkyl or (halo- substituted phenyl) alkyl group having from 1 to 6 carbon atoms in the alkyl portion, or a monocyclic heterocyclic group containing from 5 to 7 ring atoms.

In formula (VIIIA) above X is a substituted amino group. Preferred substituents are those which are readily removed to leave an unsubstituted amino group, without affecting the remainder of the molecule. Examples of suitable substituted amino groups of this type include triphenylmethylamino (the triphenylmethyl group being removable by catalytic hydrogenation or by treatment with acid); t-butoxycarbonylamino (removable by treatment with anhydrous acid) and trichloroethoxycarbonylamino (removable by reduction with zinc and acetic acid).

Another preferred group of substituted amino groups include mono acylamino groups particularly those, such as phenoxyacetamido, α-amino-phenylacetamido, 2- or 3- thienylacetamido, α-azidophenyl-acetamido, etc., which are found in the antibacterially active penicillins or cephalosporins.

In formula (VIIIA) the group R may for example be ethyl, n- or iso- propyl, n-, sec, or tert-butyl, cyclopropyl, cyclobutyl, cyclohexyl, tetrahydropyranyloxymethyl, phenyl, p- fluoro-, bromo- or chloro- phenyl, benzyl, phenylethyl or tetrahydropyranyl.

Compounds of formula (VIIIA) above wherein the sterochemistry of the azetidin ring is that shown in formula (IA¹) and wherein R³ is a carboxylic acid group or a salt thereof or an ester which is readily hydrolysable in the body e.g. acetoxymethyl or pivaloyloxymethyl, and wherein X is an acylamino group, are usually antibacterially active. A few of the remaining compounds of formula (IA¹) have some degree of antibacterial activity, but their principal use is as intermediates for conversion to antibacterially active cephalosporin analogues (substituted ceph-3-ems).

The principal novelty of the compounds of formula (I) above lies in the identity of the group R. Until now, the range of reactions which permitted modification of the nucleus of the naturally occurring cephalosporins at the 3-position of the sulphur-containing ring was somewhat limited. Compounds of formula (VIIIA) can be prepared by the process described in Part C of this specification, followed, where necessary by conversion of the carboxylic ester group in the 4-position of the cephem ring system to the desired, carboxylic acid, or salt or ester of a carboxylic acid group R³. Some of the compounds (VIIIA) may be prepared by removing the amino-substituent(s) from the group X of another member of the class (VIIIA) and acylating the resultant free amino group. This latter process is described in the ensuing Part E.

PART E

In Part D of this specification we described a class of novel substituted ceph-3-em derivatives which has a substituted amino group in the 7-position of the ceph-3-em ring system. The corresponding compounds which have a free amino group in the 7-position of the ceph-3-em ring are useful; intermediates for the preparation of antimicrobially active cephalosporin analogues.

These useful intermediates are compounds of formula (VIIIB) and acid addition salts thereof:

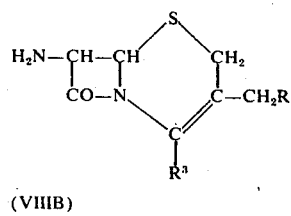

(VIIIB)

wherein R³ is a carboxylic acid group or a salt or ester of a carboxylic acid group; and R is a $C_2$ to $C_{10}$ alkyl or substituted alkyl group, a phenyl or halo- substituted phenyl group, a phenylalkyl or (halo- substituted phenyl) alkyl group having from 1 to 6 carbon atoms in the alkyl portion, or a monocyclic heterocyclic group containing from 5 to 7 ring atoms.

In formula (VIIIA) the group R may for example be ethyl, n- or iso- propyl, n-, sec-, or tert-butyl, cyclopropyl, cyclobutyl, cyclohexyl, tetrahydropyranyloxymethyl, phenyl, p- fluoro-, bromo- or chloro- phenyl, benzyl, phenylethyl or tetrahydropyranyl.

Compounds of formula (VIIIB) may be prepared from compounds of formula (VIIIA) (described in Part D herein) by removal of the substituent from the substituted amino group X and, if desired, further modification of the group R³. The modifications which are permissible on the group R³ of compounds of formulae (VIIIA) and (VIIIB) will be readily apparent to those familiar with penicillin and cephalosporin chemistry, e.g. removal of the ester group to give a free acid, conversion of the free acid group to a salt or new ester derivative.

The intermediates (VIIIB) are useful in a process for the preparation of cephalosporin analogues of formula (VIIIC):

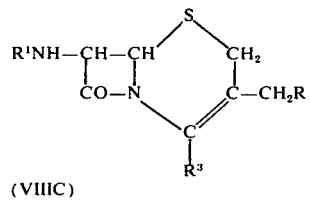

(VIIIC)

wherein R¹ is an organic acyl group; R is a lower alkyl or substituted alkyl phenyl or substituted phenyl, benzyl or substituted benzyl group; R³ is a carboxylic acid group or a salt, ester or thioester derivative of a carboxylic acid group; which process comprises reacting a compound of formula (VIIIB) above or an acid addition salt or silyl derivative thereof with a reactive acylating derivative of the appropriate acid (XII):

R'OH  (XII)

and, if silylated derivative of a compound of formula (VIIIB) was employed, removing the silyl group by alcoholysis or hydrolysis to form the desired compound of formula (VIIIB).

By the term "silyl derivative" of compound (VIIIB) we mean the product of the reaction between compound (VIIIB) and a silylating agent such as a halotrialkyl silane, a dihalodialkylsilane, a halotrialkoxysilane, a dihalodialkoxysilane or a corresponding aryl or aralkyl silane and compounds such as hexamethyldisilazane. In general halotrialkylsilanes are preferred, especially trimethylchlorosilane. The silyl derivatives of compound (VIIIB) are extremely sensitive to moisture and hydroxylic compounds, and after reaction with the reactive acylating derivative of compound (XII), the silyl group of the intermediate acylated compound can be removed by hydrolysis or alcoholysis.

In formulae (VIIIB) (VIIIC) and (XII) above, the group R¹ is an organic acyl group. Suitable acyl groups include those which are found on the antibacterially active penicillins and cephalosporins (including the semi-synthetic penicillins and cephalosporins) These include phenylacetyl and 3-thienylacetyl and phenoxyacetyl.

The reaction conditions for carrying out the process of this invention are all analogous to the conditions used in the preparation of the semi-synthetic penicillins and cephalosporins. Thus, suitable reactive derivatives of the acid (IV) include acid halides, e.g. the chloride or bromide, anhydride, mixed anhydrides and the reactive intermediates formed from the acid and a carbodiimide or a carbonyldiimidazole. Clearly, if a reactive group such as an amino group is present in the radical R¹, (as in the case of the α-aminophenylacetyl group) this will have to be protected during the course of the reaction, In such a case, any of the protecting groups known from the literature on the synthesis of α-aminobenzylpenicillin or α-aminobenzyl cephalosporins may be employed.

The following Examples illustrate the present invention. In each of these Examples where an azetidin-2-one ring is shown the stereochemical configuration of the ring is the same as that found in the naturally occurring antibacterially active penicillins (namely the configuration shown in formula (IA¹) above).

EXAMPLE 1 i. Preparation of t-butyl 3-β-phenylethyl-7-triphenylmethylamino-3-cephem-4-carboxylate (XXIII)

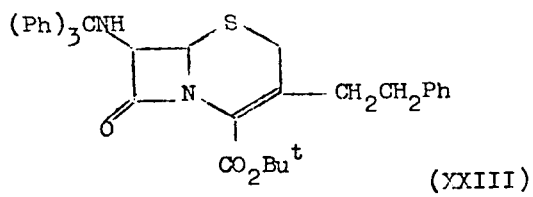

(XXIII)

4-(4-phenyl-2-oxobutylsulphinyl)-1-(1 -t-butoxycarbonyl-1-triphenylphosphoranylidenemethyl)-3-(triphenylmethyl-amino) azetidin-2-one (200 mg) was refluxed in dry dioxan (5 ml) under nitrogen for 8 hours. The mixture was evaporated to give a foam. The crude foam was chromatographed on silica gel eluting with ethyl acetate/petroleum ether mixtures to give t-butyl 3-β-phenylethyl-7-triphenylmethylamino-3-cephem-4-carboxylate-1-oxide as a yellow solid (87 mg).

$\nu_{max}$ (CHCl₃) 1785, 1720 cm⁻¹

This sulphoxide (87 mg) was dissolved in dimethylformamide (1 ml) and cooled to 0°C. Triphenylphosphine (74 mg) and acetyl chloride (33 mg) were added and the mixture stood at 0°–5°C for 4 hours. The mixture was diluted with ethyl acetate (25 ml) and washed successively with dilute sodium bicarbonate solution and brine. The dried (MgSO₄) organic layer was evaporated to give a gum. The gum was chromatographed on silica gel to give the desired cephem (XXIII) as a solid foam (77 mg).

$\nu_{max}$ (CHCl₃) 1775 cm⁻¹ (β-lactam); 1715 cm⁻¹ (ester) σppm (CDCl₃) 1.51 (5.9H); 2.4–3.2 (m.7H.1 H exchanges with D₂O); 4.19 (d.1H. J=5Hz); 4.5–4.9 (m.1H); 7.0–7.9 (Aromatics).

ii. Preparation of t-butyl 3-β-phenylethyl-7-(2-thienylacetamido)-3-cephem-4-carboxylate (XXIV)

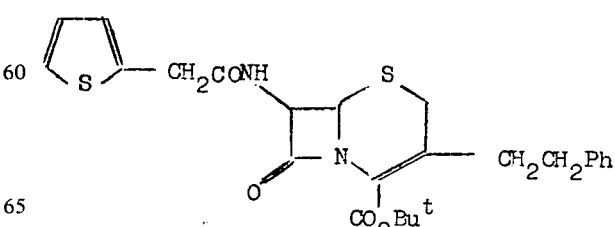

(XXIV)

The cephem (XXIII) (77 mg) was dissolved in acetone (1 ml) and cooled to 0°C. p-Toluene sulphonic acid monohydrate (24 mg) was added and the mixture was stood at 0°C for 1 hour. The mixture was then allowed to attain room temperature and was stood at room temperature for 6 hours. The mixture was evaporated. The residue was suspended in ethyl acetate (20 ml) and shaken with saturated sodium bicarbonate solution (5 ml). The organic layer was separated and washed with brine. The dried (MgSO$_4$) organic layer was evaporated to give t-butyl 3-$\beta$-phenylethyl-7-amino-3-cephem-4-carboxylate (XXV) contaminated with triphenylmethanol as a solid (61 mg).

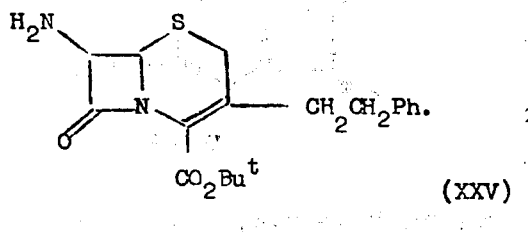

The crude free base (XXV) (61 mg) was dissolved in dry methylene chloride (2 ml) and cooled to −10°C. To the stirred, cooled solution was added triethylamine (50 mg) and 2-thienylacetyl chloride (freshly distilled, 30 mg). The mixture was stirred at −10°C for 15 minutes. The mixture was diluted with methylene chloride (10 ml) and washed with brine. The dried (MgSO$_4$) organic layer was evaporated to give a gum.

The gum was chromatographed on silica gel eluting with ethyl acetate/petroleum ether mixtures to give the desired cephem (XXIV) as a solid foam (30 mg, 49%).

$\nu_{max}$(CHCl$_3$) 1785 cm$^{-1}$ ($\beta$-lactam); 1720 cm$^{-1}$ (ester); 1690 cm$^{-1}$ (amide).

Molecular Ion measured at 484.1512 (C$_{25}$H$_{28}$N$_2$O$_4$S$_2$ requires 484.1490, Error = 4.5 ppm). Fragmentation was consistent with structure.

iii. Preparation of 3-$\beta$-phenylethyl-7-(2-thienylacetamido)-3-cephem-4-carboxylic acid (XXVI)

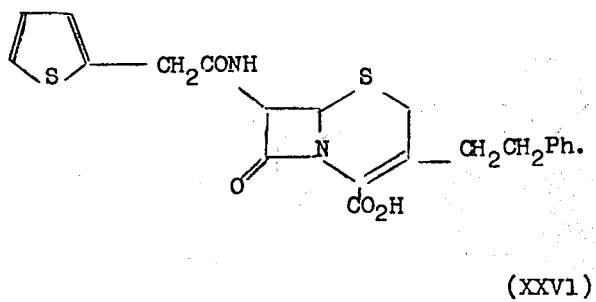

The cephem (XXIV) (29 mg) was dissolved in trifluoroacetic acid (0.5 ml) and the solution was stood at room temperature for 30 minutes. The solution was evaporated and the residual gum re-evaporated from dry benzene (4 × 1 ml). The residual gum was dissolved in dry ether and evaporated to give the desired cephem carboxylic acid (XXVI) as a dark yellow solid foam (24 mg, 94%).

$\mu_{max}$(CHCl$_3$) 1775 cm$^{-1}$ ($\beta$-lactam); 1675 cm$^{-1}$ (amide).

The minimum inhibitory concentrations (MIC) of this compound against five typical Gram-positive bacteria are tabulated below:

| Organism | MIC ($\mu$g/ml in agar) |
|---|---|
| B.subtilis | 0.05 |
| Staph.aureus Oxford | 0.05 |
| Staph.aureus Russell | 1.5 |
| $\beta$-haemolytic Strep.CN10 | 0.02 |
| Strep.pneumoniae CN33 | 0.15 |

EXAMPLE 2 i. Preparation of Methyl 3-benzyl-7-tritylamino-3-cephem-4-carboxylate. (I)

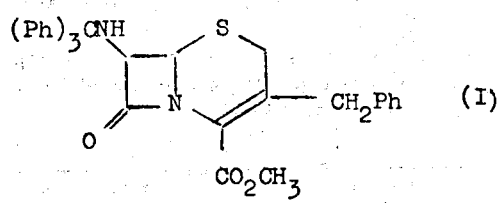

1-(Methoxycarbonyl-1-triphenylphosphoranylidenemethyl)-3-(triphenylmethylamino)-4-(3-phenyl-2-oxopropylthio)azetidin-2-one (135 mg) was gently refluxed in dry dioxan (20 ml) for 60 hours under nitrogen. Evaporation of the solvent and chromatography of the residue on silica gave (I) as a white solid (66 mg). Crystallisation from methanol yielded white plates m.p. 163°, $\nu_{max}$(CHCl$_3$) 3480.(NH), 1775 ($\beta$-lactam), 1720 (ester), 1630 (double bond) cm$^{-1}$ $\sigma$ppm (CDCl$_3$) 2.98 (d.1H, J=10Hz, D$_2$O exchanged), 3.07 (s.2H), 3.77 (centre of AB quartet, J=15Hz), 3.83 (s,3H), 4.3(d, 1H, J=5 Hz), 4.71 (q, 1H, J=5Hz, 10Hz, collapsing to a doublet, J=5Hz, on D$_2$O exchange), 7.1 - 7.7 (m, 20H).

ii. Preparation of Methyl 3-benzyl-7-phenoxyacetamido-3-cephem-4-carboxylate (II)

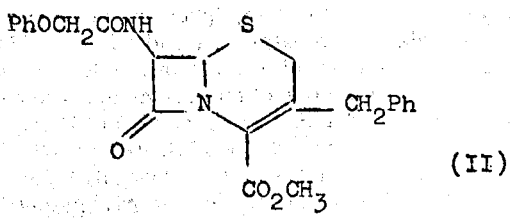

Methyl 3-benzyl-7-tritylamino-3-cephem-4-carboxylate (111 mg) was dissolved in acetone (1.5 ml.) and the solution cooled to −20°. p-Toluene sulphonic acid (40 mg) in acetone (0.5 ml) was added dropwise over a few minutes and the solution left at 0° for 16 hours. Thin layer chromatography (TLC) still showed some unchanged starting material was present. A further quantity of p-toluene sulphonic acid (10 mg) was added and the solution left at room temperature for 4 hours. Ethyl acetate was added and the solution washed with dilute aqueous sodium bicarbonate and brine. Evaporation of the dried organic layer afforded methyl 3-benzyl-7-amino-7-cephem-4-carboxylate contaminated with trityl alcohol.

The crude methyl 3-benzyl-7-amino-3-cephem-4-carboxylate was dissolved in dry dichloromethane (3 ml.) and the solution cooled to −20°. Dry triethylamine (22 mg) in dichloromethane (0.5 ml) was added followed by phenoxyacetyl chloride (36 mg) in dichloromethane (0.5 ml). After 15 minutes the solution was washed with water (× 2), dried and evaporated. Chromatography on silica afforded methyl 3-benzyl-7-phenoxyacetamido-3-cephem-4-carboxylate (II) as a white solid (61 mg). A sample recrystallised from ethyl acetate/60°–80° petroleum ether had m.p. 161°–162°.

$\nu_{max}$(Nujol) 3215, 1775, 1718, 1670, 1625 cm$^{-1}$.

σ ppm (CDCl$_3$) 3.27 (AB quartet, J = 19Hz), 3.83 (AB quartet, J= 15 Hz), 3.9 (s, 3H), 4.57 (s, 2H), 5.03 (d, 1H, J= 5Hz), 5.88 (q, 1H, J= 5Hz, 10Hz), 6.8—7—5 (m, 11H).

The minimum concentrations of this compound required to inhibit growth of five typical Gram-positive bacteria are tabulated below.

| Organism | M.I.C. (μg/ml)AGAR |
| --- | --- |
| B.subtilis | 1.95 |
| Staph. aureus Oxford | 0.98 |
| Staph. aureus Russell | 15.6 |
| β-haemolytic Strep.CN10 | 1.95 |
| Strep. pneumoniae CN33 | 0.98 |

EXAMPLE 3 i. Preparation of t-Butyl 3-benzyl-7-triphenylmethylamino-3-cephem-4-carboxylate (III)

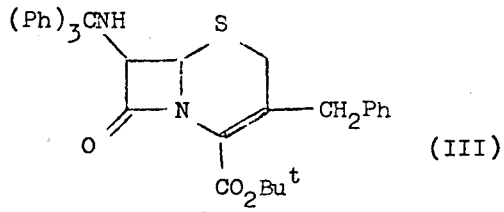

(III)

1-(1-t-Butoxycarbonyl-1-triphenylphosphoranylidenemethyl)-3-(triphenylmethylamino)-4-(3-phenyl-2-oxopropylthio) azetidin-2-one (331 mg) was refluxed in dry dioxan (15 ml) under nitrogen for 25 hours. Evaporation of the solvent and chromatography of the residue on silica gave (III) (141 mg).

$\nu_{max}$(CHCl$_3$) 3480, 1775, 1710, 1630 cm$^{-1}$

σ ppm (CDCl$_3$) 1.5 (s.9H), 2.95 (d.1H. J= 10Hz, D$_2$O exchange), 3.00 (centre of AB quartet), 3.68 (centre of AB quartet, J= 15Hz), 4.25 (d. 1H. J= 5Hz), 4.70 (q. 1H, J= 5Hz, 10Hz, collapsing to a doublet, J= 5Hz, on D$_2$O exchange, 7.1–7.7 (m, 20H).

ii. Preparation of t-Butyl 3-Benzyl-7-[2-(thienyl) acetamido]-3-cephem-4-carboxylate (IV)

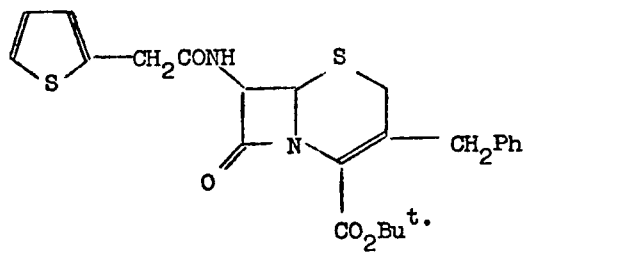

(IV)

t-Butyl 3-benzyl-7-triphenylmethylamino-3-cephem-4-carboxylate (929 mg) was dissolved in acetone (2 ml) and the solution cooled to −20°. p-Toluene sulphonic acid (330 mg) in acetone (2 ml) was added dropwise over 2 – 3 minutes and the solution left at 0° for 18 hours. The crystalline product was filtered, washed with a little cold acetone and dried (493 mg) m.p. 175°–177°. The mother liquors were taken up in ethyl acetate, washed with dilute aqueous sodium bicarbonate and brine, dried and evaporated. Chromatography on silica gave crystalline t-butyl 3-benzyl-7-amino-3-cephem-4-carboxylate (V).

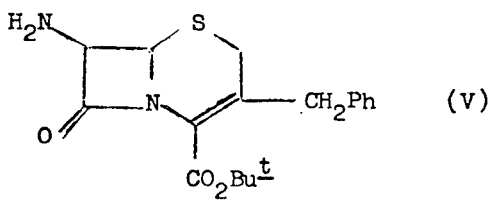

$\nu_{max}$(Nujol) (p-toluene sulphonate of (VI) 1778, 1720, 1640 cm$^{-1}$ $\nu_{max}$(Nujol) (V as free base) 3400, 3325, 1764, 1710, 1640 cm$^{-1}$ σ ppm (CDCl$_3$) (V as free base) 1.58 (s, 9H), 1.73 (broad singlet, 2H, D$_2$O exchanged), 3.25 (centre of AB quartet, J= 19Hz), 3.77 (centre of AB quartet, J= 15Hz) 4.7 (d, 1H, J= 5Hz), 4.95 (d, 1H, J= 5Hz), 7.3 (s, 5H).

The p-toluene sulphonic acid salt of V (76 mg) was suspended in dry methylene chloride (5 ml) at −20°. Dry triethylamine (60 mg) was added followed by 2-thienylacetyl chloride (25 mg). The reaction mixture was washed with water, dried and evaporated. Chromatography on silica gave IV which crystallised on trituration with ether (44 mg).

$\nu_{max}$(CHCl$_3$) 3330, 1778, 1710, 1680, 1630 cm$^{-1}$ iii. Preparation of 3-Benzyl-7-[2-thienyl)acetamido]-3-cephem-4 carboxylic acid VI

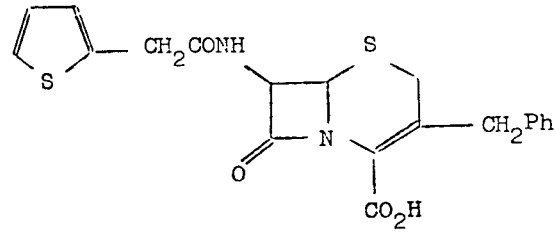

(VI)

t-Butyl 3-benzyl-7-[2-(thienyl)acetamido]-3-cephem-4-carboxylate (IV) (44 mg) was dissolved in anhydrous trifluoroacetic acid (0.5 ml). After 1 hour at room temperature, the solvent was removed under reduced pressure, toluene was added and the mixture repeated. This was repeated twice more to give (VI) as a pale yellow foam.

The minimum inhibitory concentrations (MIC) of this compound required to inhibit growth of five typical Gram-positive bacteria are tabulated below.

| Organism | MIC ($\mu$g/ml) Agar |
|---|---|
| B.subtlis | 0.2 |
| Staph. aureus Oxford | 0.05 |
| Staph. aureus Russell | 10 |
| $\beta$-haemolytic Strep.CN10 | 0.2 |
| Strep.pneumoniae CN33 | 0.2 | iv. Preparation of
3-Benzyl-7-[D-$\alpha$-aminopheylacetamido]-3-cephem-4-carboxylic acid (VII: R=H)

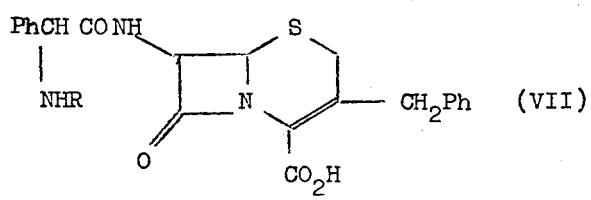

METHOD A

N-methylmorpholine (1 microdrop) was added to sodium N-(1-methoxycarbonylpropen-2-yl)-D-$\alpha$-aminophenylacetate (182 mg) in dry acetone (3 ml) and the suspension cooled to $-15°$. Ethyl chloroformate (73 mg) in dry acetone (1.5 ml) was added and the mixture stirred for 30 minutes. The mixture was then added to t-butyl 3-benzyl-7-amino-3-cephem-4-carboxylate (212 mg) in dry acetone (4 ml) at $-15°$. After stirring for 1 hour with no further external cooling, the solvent was removed under reduced pressure and the residue taken up in ethyl acetate. The solution was washed with aqueous sodium bicarbonate and brine, dried and evaporated. Chromatography on silica afforded unchanged starting material (124 mg) and the N-protected derivative (VII; R=CH$_3$C$_1$=CHCO$_2$CH$_3$) (115 mg).

$\nu_{max}$ 3390, 3250, 1782, 1718, 1650, 1610 cm$^{-1}$.

The latter was dissolved in anhydrous trifluoroacetatic acid (2 ml) and the solution was left at room temperature for 35 minutes. The solvent was removed under reduced pressure and toluene was added and the mixture re-evaporated. This was repeated twice more and the residue triturated with ether to give the trifluoroacetic acid salt of (VII; R=H) as a pale yellow solid (60 mg). This was taken up in 10% aqueous methanol (5 ml) at $-0°$ and the pH adjusted to 4.5 with 10% triethylamine/methanol. The solvent was removed under reduced pressure and the residue triturated with ether/methanol. The solid was filtered off to give (VII; R = H) (18 mg), after drying in vacuo.

$\nu_{max}$ (Nujol) 3200, 1780 sh, 1768, 1690 1600 cm$^{-1}$.

METHOD B a. Preparation of t-Butyl
7$\beta$[N-(t-butoxycarbonyl)D-$\alpha$-phenylglycylamido]3-benzyl-3-cephem-4-carboxylate VIII

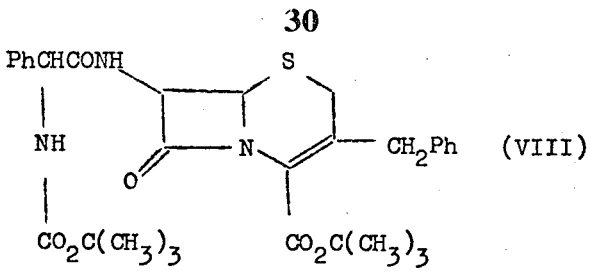

To a solution of re-distilled methyl chloroformate (100 mg) in dry tetrahydrofuran (15 ml) cooled at $-10°$ in a carbon tetrachloridecardice bath, were added, dropwise and with stirring N-(t-butoxycarbonyl)-D-$\alpha$-phenylglycine (261 mg), triethylamine (105 mg : 0.14 ml) and dimethylbenzylamine (1 drop) in dry tetrahydrofuran (10 ml) over 5 minutes. Twenty-five minutes following addition, t-butyl 3-benzyl-7-amino-3-cephem-4-carboxylate (330 mg; regenerated from the p-toluene sulphonate salt) in dry tetrahydrofuran (5 ml) was added dropwise over 5 minutes. The mixture was stirred at $-10°$ for a further 2 hours. The precipitated triethylamine hydrochloride was filtered off and the filtrate evaporated in vacuo. The residual oil was dissolved in ethyl acetate for successive cold washes with water, 5% hydrochloric acid, 5% aqueous sodium bicarbonate solution, and water. The dried (MgSO$_4$) ethyl acetate solution was evaporated and the residue chromatographed on silica to give (VIII) as a white crystalline solid (461 mg) m.p. 152°–153° (ether/petroleum ether).

$\nu_{max}$(Nujol) 3290, 1772, 1708, 1685, 1664 cm$^{-1}$.

$\sigma$ ppm (CDCl$_3$) 1.42 (s,9H), 1.55 (s,9H), 3.17 (centre of AB quartet, J = 18Hz), 3.78 (centre of AB quartet, J = 14.5Hz), 4.94(d, J = 5Hz, C$_6$ - H), 5.22 (d, $\alpha$ - CH), 5.72 (q and d, 2H, C$_7$ - H and amide NH), 6.66 (d, J = 9Hz, amide NH), 7.17–7.45 (d, 10H).

C$_{31}$H$_{37}$O$_6$N$_3$S requires C, 64.21; H, 6.43; N, 7.25; S, 5.53. Found C, 64.47; H, 6.41; N, 7.13; S, 5.63.

b. Preparation of
7$\beta$-[(D-$\alpha$-aminophenylacetamido]-3-benzyl-3-cephem-4-carboxylic acid (VII; R = H)

t-Butyl 7 N-(tert-butoxycarbonyl)D-$\alpha$-phenylgylcylamido-3-benzyl-3-cephem-4-carboxylate (VIII) (220 mg) was dissolved in anhydrous trifluoroacetic acid (7 ml). After 30 minutes at room temperature the solvent was evaporated in vacuo. Dry toluene (5 ml) was added and the solvent re-evaporated. This was repeated twice more. The residue was triturated with ether and the solid filtered to give the trifluoroacetic acid salt of (VII; R = H) (201 mg). Some of the latter (98 mg) was dissolved in water at 5°–10°. After 15 minutes the solid that had separated was filtered, washed with methylene chloride and ether and dried in vacuo to give (VII; R = H) (57 mg).

$\nu_{max}$(KBr) 3415, 3180, 3020, 1758, 1682, 1580 (broad) cm$^{-1}$.

$\nu_{max}$(Nujol) 3230, 1780, 1760 (shoulder), 1692, 1642 (sh), 1590, 1570 (sh.) cm$^{-1}$.

The minimum inhibitory concentrations (MIC) of this compound required to inhibit the growth of five typical Gram-positive bacteria are tabulated below:

| Organism | MIC ($\mu$g/ml in agar) |
|---|---|
| B.subtlis | 0.25 |
| Staph. aureus Oxford | 0.1 |
| Staph. aureus Russell | 2.5 |
| -62 -haemolytic Strep.CN10 | 0.1 |
| Strep.pneumoniae CN 33 | 1.0 |

EXAMPLE 4 i. Preparation of t-Butyl 3-p-fluorobenzyl-7-triphenyl-methylamino-3-cephem-4-carboxylate (IX)

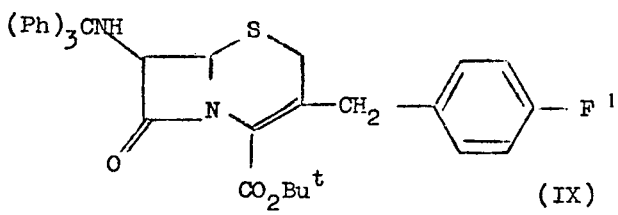

(IX)

1-(1-t-butoxycarbonyl-1-triphenylphosphoranylidenemethyl)-3-(triphenylmethylamino)-4-(3-p-fluorophenyl-2-oxopropylthio)azetidin-2-one (253 mg) was refluxed in dry dioxan (25 ml) under nitrogen for 24 hours. Evaporation of the solvent and chromatography of the residue on silica gave (IX) as a white solid (131 mg).

$\nu_{max}$(CHCl$_3$) 1775, 1715 cm$^{-1}$ $\sigma$ ppm (CDCl$_3$) 1.52 (s,3H), 3.01 (q, J = 17 Hz, 2H), 2.66 −3.12 (1H, exchange D$_2$O, 3.63 (q, J = 15Hz, 2H). 4.28 (d, J = 4.5Hz, 1H), 4.71 (multiplet collapsing to d, J = 4.5Hz on D$_2$O exchange, 1H), 6.77–7.58 (m, aromatic).

ii. Preparation of t-Butyl 3-p-fluorobenzyl-7-(2-thienylacetamido)-3-cephem-4-carboxylate (X)

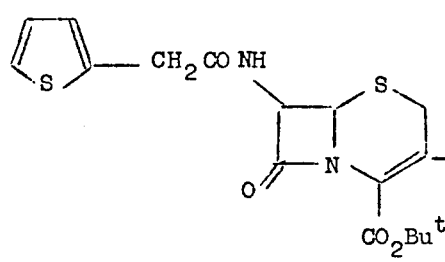

(X)

t-Butyl 3-p-fluorobenzyl-7-triphenylmethylamino-3-cephem-4-carboxylate (IX) (72 mg) was dissolved in acetone and the solution cooled to 0°. p-Toluene sulphonic acid (25 mg) in acetone (0.5 ml) was added dropwise over a few minutes and the solution left to warm to room temperature with stirring. After 2.5 hours a solid had formed but t.l.c. still showed some unchanged (IX) to be present. The mixture was again cooled to 0° and a further quantity of p-toluene sulphonic acid (5 mg) in acetone added. After leaving at room temperature for a further 1.5 hours, the white solid was filtered off. This solid was suspended in ethyl acetate and treated with saturated sodium bicarbonate solution. The organic layer was washed with brine, dried and evaporated to give t-butyl 7-amino-3-p-fluorobenzyl-3-cephem-4-carboxylate (XI) (28 mg) shown to be pure by t.l.c.

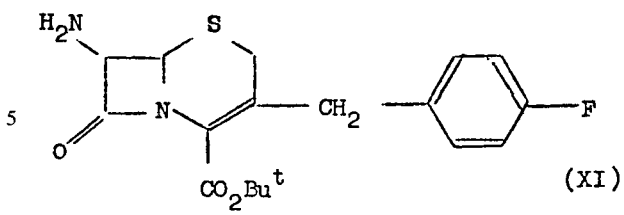

(XI)

The free base (XI) (80 mg) was treated with 2-thienylacetyl chloride (40 mg) and triethylamine (0.05 ml) in dry methylene chloride (5 ml) at −20°. After 15 minutes the solution was washed with brine, dried and evaporated. Chromatography on silica gave the cephem (X) (50 mg) which crystallised on trituration with dry ether.

$\nu_{max}$(CHCl$_3$) 3380, 1780, 1710, 1685 cm$^{-1}$ iii. Preparation of 3-p-fluorobenzyl-7-(2-thienylacetamido)-3-cephem-4-carboxylic acid (XII)

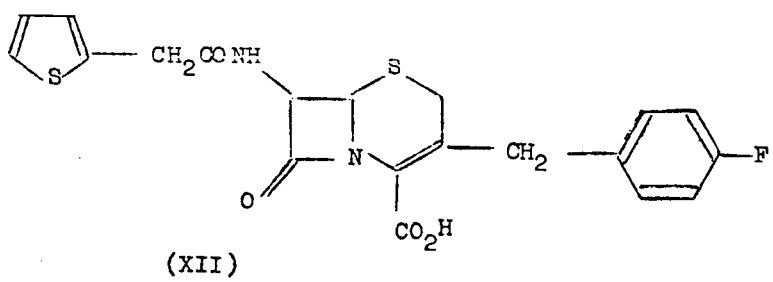

(XII)

t-Butyl 3-p-fluorobenzyl-7-(2-thienylacetamido)-3-cephem-4-carboxylate (X) (36 mg) was treated with trifluoroacetic acid (5 ml) at room temperature for 40 minutes. The excess trifluoroacetic acid was distilled off azeotropically with dry benzene to give the free acid (XII) as a foam $\nu_{max}$(CHCl$_3$) 1770, 1705, 1680 cm$^{-1}$ The minimum inhibitory concentrations (MIC) of this compound required to inhibit the growth of five typical Gram-positive bacteria are tabulated below:

| Organism | MIC ($\mu$g/ml in agar) |
| --- | --- |
| B.subtlis | 0.5 |
| Staph. aureus Oxford | 0.25 |
| Staph. aureus Russell | 10 |
| $\beta$-haemolytic Strep.CN10 | 0.25 |
| Strep.pneumoniae.CN33 | 0.25 | iv. Preparation of t-butyl 3-p-fluorobenzyl-7-carboxymethylthioacetamido-3-cephem-4-carboxylate (XIII)

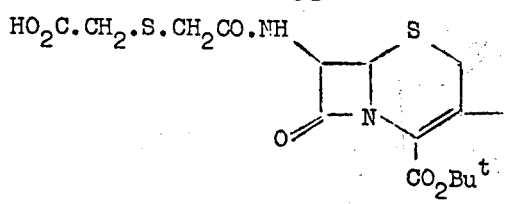
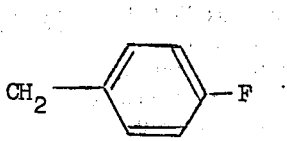

(XIII)

To the free base (XI)

To t-butyl 7-amino-3-p-fluorobenzyl-3-cephem-4-carboxylate (28 mg) in dry methylene chloride at 0° was added dropwise thiodiacetic anhydride (9 mg) in methylene chloride. After 20 minutes evaporation of the solvent gave (XIII), which was obtained as an amorphous solid on re-evaporation from dry ether.

$\nu_{max}$(CHCl$_3$) 1770, 1715, 1680 cm$^{-1}$ v. Preparation of 3-p-fluorobenzyl-7-carboxymethylthioacetamido-3-cephem-4-carboxylate (XIV)

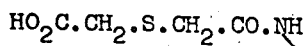
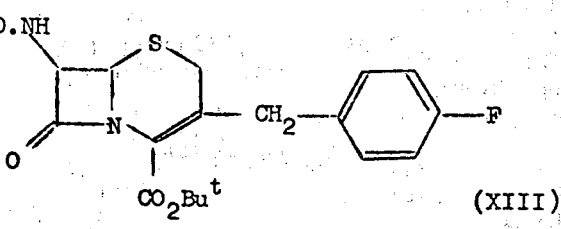

(XIII)

The total crude cephem (XIII) from (iv) above was treated with trifluoroacetic acid (3 ml) at room temperature for 1 hour. The excess trifluoroacetic acid was distilled off azeotropically with dry benzene to give the acid (XIV) characterised as the triethylamine salt.

$\nu_{max}$(CHCl$_3$) 3280, 1770, 1670 cm$^{-1}$

The minimum inhibitory concentrations (MIC) of the free acid (XIV) required to inhibit the growth of five typical Gram-positive bacteria are tabulated below:

| Organism | MIC ($\mu$g/ml in agar) |
|---|---|
| B.subtilis | 100 |
| Staph.aureus Oxford | 5.0 |
| Staph.aureus Russell | 50 |
| $\beta$-haemolytic Strep.CN.10 | 25 |
| Strep.pneumoniae.CN33 | 25 |

EXAMPLE 5 i. Preparation of t-Butyl 3-ethyl-7triphenylmethylamino-3-cephem-4-carboxylate (XV)

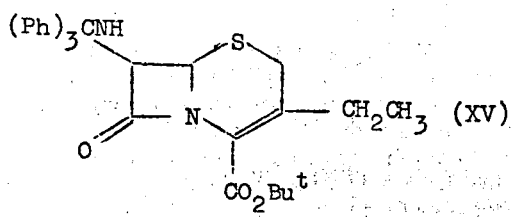

1-(1-t-butoxycarbonyl-1-triphenylphosphoranylidenemethyl)-3-(triphenylmethylamino)-4-(2-oxobutylthio)azetidin-2-one sulphoxide (0.31 g)

was refluxed in dry dioxan (20 ml) under nitrogen for 18 hours. Evaporation of the solvent and chromatography of the residue on silica gave t-butyl 3-ethyl-7-triphenylmethylamino-3-cephem-4-carboxylate-1-oxide (0.10g) as a gum $\nu_{max}$(CHCl$_3$) 1780, 1712, 1620 cm$^{-1}$ This sulphoxide (98 mg) in dimethylformamide (5 ml) at 0° was treated with triphenylphosphine (95 mg) and acetyl chloride (45 mg). The mixture was left overnight at 5°. After dilution with ethyl acetate the organic phase was washed with saturated aqueous sodium bicarbonate then brine, dried and evaporated. Chromatography on silica gave the sulphide (XV) as a white amorphous solid (53 mg).

$\nu_{max}$(CHCl$_3$) 1770, 1710, 1630 cm$^{-1}$ $\sigma$ ppm (CDCl$_3$) 1.07 (t, J = 7.5Hz, 3H), 1.54 (s,9H), 2.27 (q, J = 7.5Hz, 2H) 2.9 (broad, 1H exchange D$_2$O), 3.15 (s,2H), 4.23 (d, J = 4.5Hz, 1H), 4.67 (broad, giving d, J = 4.5Hz on D$_2$O exchange, 1H), 7.13–7.6 (ar.).

ii. Preparation of t-butyl 3-ethyl-7-(2-thienylacetamido)-3-cephem-4-carboxylate (XVI)

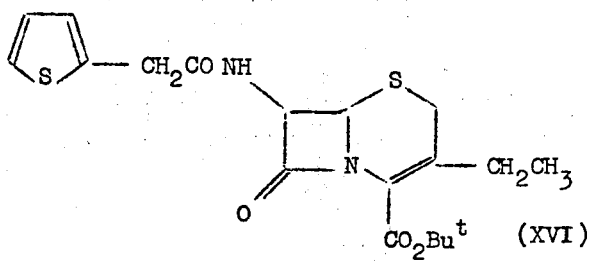

(XVI)

t-Butyl 3-ethyl-7-triphenylmethylamino-3-cephem-4-carboxylate (53 mg) was dissolved in acetone and the solution cooled to −20°. p-Toluene sulphonic acid (21 mg) in acetone was added and the mixture warmed to room temperature. After 1 hour crystals had formed but t.l.c. showed some unchanged starting material to be present. The mixture was re-cooled to −10° and a further quantity of p-toluene sulphonic acid added (5 mg). After a further 2 hours at room temperature the solvent was removed leaving a residue containing trityl alcohol and the p-toluene sulphonate of t-butyl 3-ethyl-7-amino-3-cephem-4-carboxylate.

This residue was suspended in dry methylene chloride and triethylamine (40 mg) added. The solution obtained was cooled, −20°, and freshly distilled 2-thienylacetyl chloride (26 mg) in methylene chloride added dropwise with stirring, over about 5 minutes. After 15 minutes the solution was washed with brine, dried and evaporated. Chromatography on silica gave the cephem (XVI) (23 mg). $\nu_{max}$(CHCl$_3$) 3380, 1780, 1710, 1685, 1630 cm$^{-1}$ iii. Preparation of 3-ethyl-7-(2-thienylacetamido)-3-cephem-4-carboxylic acid (XVII)

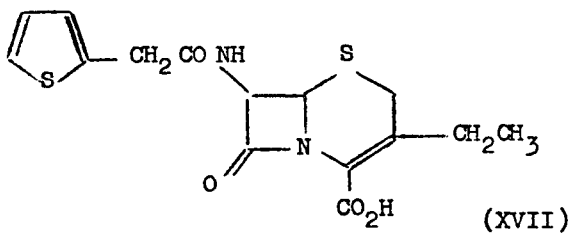

(XVII)

t-Butyl 3-ethyl-7-(2-thienylacetamido)-3-cephem-4-carboxylate (23 mg) was treated with trifluoroacetic acid at room temperature for 1 hour. The excess trifluoroacetic acid was distilled off azeotropically with dry benzene to give the free acid (XVII) as a gum (17 mg) $\nu_{max}$(CHCl$_3$) 1770, 1705, 1680 cm$^{-1}$ The minimum inhibitory concentrations of this compound required to inhibit the growth of five typical Gram-positive bacteria are tabulated below:

| Organism | MIC ($\mu$g/ml in agar) |
|---|---|
| B.subtlis | 2.5 |
| Staph.aureus Oxford | 2.5 |
| Staph.aureus Russell | 2.5 |
| $\beta$-haemolytic Strep.CN10 | 2.5 |
| Strep.pneumoniae.CN33 | 2.5 |

EXAMPLE 6

Preparation of t-Butyl 3-2'-tetrahydropyranyloxyethyl)-7-triphenylmethylamino-3-cephem-4-carboxylate (XVIII)

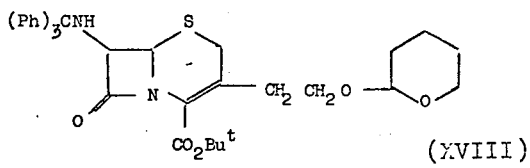

(XVIII)

1-(1-t-butoxycarbonyl-1-triphenylphos-phoranylidenemethyl)-3-(triphenylmethylamino)-4-(4-tetrahydropyranyloxy-2-oxobutylthio)azetidin-2-one (220 mg) was refluxed under nitrogen in dry dioxan (10 ml) for 47 hours. Evaporation of the solvent and chromatography of the residue on silica gave (XVIII) (102 mg)
$\nu_{max}$(CHCl$_3$) 1770, 1708, 1625 cm$^{-1}$

EXAMPLE 7 i. Preparation of tert-butyl 3-(2-tetrahydropyranylmethyl)-7-triphenylmethylamino-3-cephem-4-carboxylate (XIX)

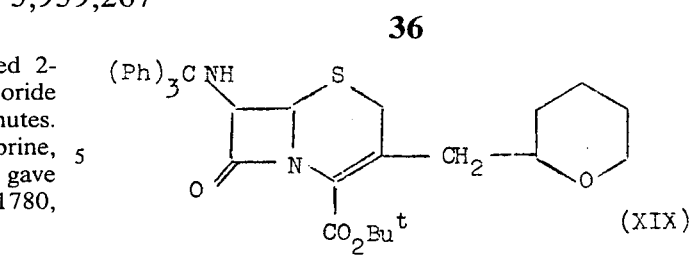

(XIX)

1(1-t-butoxycarbonyl-1-triphenylphos-phoranylidenemethyl)-3-triphenylmethylamino)-4-[3-(2-tetrahydropyranyl)-prop-2-onethio]azetidin-2-one (700 mg) was taken up in dioxan (20 ml) and refluxed under nitrogen for 26 hours. The dioxan was then removed and the crude product was chromatographed on silica gel, eluting with 60 petroleum (b.p. 60°–80°λ)/ethyl acetate in 8:2, 7:3 and 6:4 mixtures. Early fractions contained the cephem (XIX) (180 mg)
$\nu_{max}$(CHCl$_3$) 1770, 1710, 1625 cm$^{-1}$
Later fractions contained recovered starting material. This was again dissolved in dioxan and refluxed for 3 days and yielded the cephem (XIX) (70 mg).

ii. Preparation of t-butyl 3-(2-tetrahydropyranylmethyl)-7-(2-thienylacetamido)-3-cephem-4-carboxylate (XX)

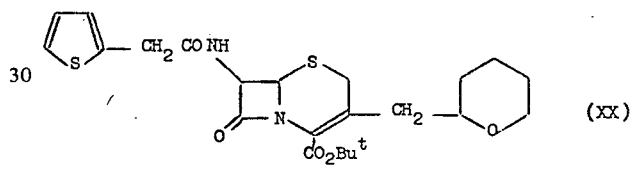

(XX)

The triphenylmethylaminocephem XIX (260 mg) was dissolved in a small quantity of acetone (ca. 3 ml) and cooled to ca.−50°. p-Toluene sulphonic acid monohydrate (91 mg) in the minimum quantity of acetone (ca.0.75 ml) was then added, and the mixture was left to stand at −10° for 18 hr, and then at room temperature for 3 hr. The acetone was evaporated off and the residue was taken up in ethyl acetate and washed with aqueous sodium bicarbonate, followed by brine. After drying (MgSO$_4$) the ethyl acetate was removed and the residue was chromatographed on silica gel, eluting with chloroform, followed by 7:3 and 3:7 mixtures of petroleum (b.p. 60°–80°) and ethyl acetate. This led to the isolation of t-butyl 3-(2-tetrahydropyranylmethyl)-7-amino-3-cephem-4 carboxylate (XXI) (120 mg) $\nu_{max}$(CHCl$_3$) 3,300 cm$^{-1}$ (—NH$_2$), 1775 cm$^{-1}$ ($\beta$-lactam C=O), 1710 cm$^{-1}$ ($\alpha$,$\beta$-unsaturated ester C=O), 1620 cm$^{-1}$(C=C).

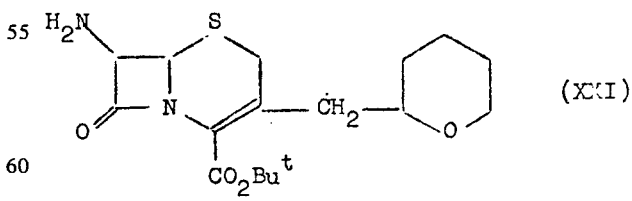

(XXI)

The free base (XXI) (120 mg) was taken up in methylene chloride (5 ml), cooled to −13° and triethylamine (0.13 ml), followed by freshly distilled 2-thienyl-acetyl chloride (100 mg) in methylene chloride (1 ml), was added to the solution. The cooled mixture was stirred for 15 minutes, brine was then added, the layers were separated, and the organic layer was dried (MgSO$_4$)

and evaporated to leave an oil. Chromatography on silica gel, eluting with petroleum (b.p. 60°–80°)/ethyl acetate (8:2 then 7:3, led to the isolation of the thienylacetamidocephem (XX) as an oil. $\nu_{max}$(CHCl$_3$) 3325 cm$^{-1}$ (NH), 1775 cm$^{-1}$ $\beta$–lactam C=O), 1710 cm$^{-1}$ ($\alpha,\beta$-unsaturated ester C=O), 1680 cm$^{-1}$ (amido C=O).

Trituration of the oil with ether gave the cephem (X) as a white solid (29 mg), m.p. 175°–185° decomp. M$^+$ m/e 478 (parent peak) and the fragmentations expected for the cephem (X).

iii. Preparation of 3-(2-tetrahydropyranylmethyl)-7-(2-thienylacetamido)-3-cephem-4-carboxylic acid (XXII)

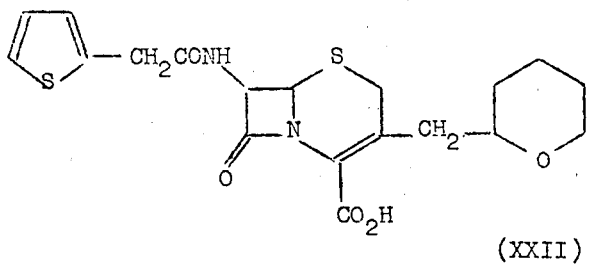

(XXII)

The cephem ester (XX) (28 mg) was dissolved in trifluoroacetic acid (0.8 ml) and allowed to stand at room temperature for 30 min. The reaction mixture was evaporated azeotropically from dry benzene to give the acid (XXII) as a glass (25 mg)

$\nu_{max}$(CHCl$_3$) 1775, 1730–1750, 1675 cm$^{-1}$

The minimum inhibitory concentrations (MIC) of this compound against five typical Gram-positive bacteria are tabulated below:

| Organism | MIC ($\mu$g/ml in agar) |
|---|---|
| B.subtlis | 0.5 |
| Staph.aureus Oxford | 0.25 |
| Staph.aureus Russell | 10 |
| $\beta$-haemolytic Strep.CN10 | 0.25 |
| Strep.pneumoniae.CN33 | 0.25 |

Preparation of starting material for Example 1 i. Benzyl 6-$\beta$-(triphenylmethylamino)penicillanate (1.64g) was stirred in dry tetrahydrofuran (60ml) containing 1-bromo-4-phenylbut-2-yne (0.69g, 1.1eq., obtained by treating the corresponding hydroxy compound with PBr$_3$) under N$_2$. A 0.778M solution of potassium t-butoxide in t-butanol (4.3 ml. diluted with 15ml tetrahydrofuran) was added over 45 minutes and stirring was continued for 1.5 hours. The work-up was carried out as before and gave a chromatographical purified 1-(1-benzyloxycarbonyl-2-methyl-1-propenyl)-3-triphenylmethylamino-4-(4-phenylbut-2-ynylthio)azetidin-2-one 639mg (32%). $\nu_{max}$ (CHCl$_3$) 1755 cm$^{-1}$ ($\beta$-lactam), 1718 cm$^{-1}$ (ester). $\sigma$ ppm (CDCl$_3$) 1.99 (s, 3H), 2.19 (s, 3H), 2.75 (m, 3H, one H exchange), 3.50 (t, 2H, J=2Hz), 4.50 (m, 1H, collapsing to doublet J=5Hz with D$_2$O), 4.81 (d, 1H, J=5Hz), 5.01 (q, 2H) 7.0–7.8 (aromatic)

ii. 1-(1-Benzyloxycarbonyl-2-methyl-1-propenyl)-3-(triphenylmethylamino)-4-(4-phenylbut-2-ynylthio)azetidin-2-one (5.40g) was dissolved in a mixture of pyridine (60ml) and water (6ml). The stirred mixture was cooled in an ice-salt bath and finely powdered potassium permanganate (2.30g) was added. The cooled mixture was stirred for a further 1.5 hours. The mixture was diluted with ethyl acetate (100ml) and water (10ml) and sulphur dioxide was passed until the manganese dioxide had dissolved. The organic layer was separated and washed successively with sodium bicarbonate solution, brine, N.hydrochloric acid, and brine The dried (MgSO$_4$) organic layer was evaporated to give a crude gum (4.8g). The crude gum was chromatographed on silica gel eluting with ethyl acetate/petroleum ether mixtures to give 4-(4-phenylbut-2-ynylthio)-3-triphenylmethylamino-azetidin-2-one as a crystalline solid (0 852g, 22%). Recrystallisation of the product gave a colourless crystalline solid, MP=145°–6°C.

$\nu_{max}$ (CHCl$_3$) 3400 cm$^{-1}$ (N-H), 1765 cm$^{-1}$ ($\beta$-lactam)

$\sigma$ ppm (CDCl$_3$) 3.05 (centre of multiplet, 3H collapsing to triplet, 2H, J=2Hz with D$_2$O); 3.57 (t, 2H, J=2Hz); 4.55 (centre of muliplet, 2H, collapsing to broad singlet with D$_2$O); 6.15 (broad S, 1H, exchanges with D$_2$O); 7.0–7.7 (aromatics).

iii. Tert-butyl glyoxalate mono hydrate (2.1g) and dry benzene (25ml) were refluxed under nitrogen with provision for removal of water until all the water had been removed. 4-(4-phenylbut-2-ynylthio)-3-(triphenylmethylamino)azetidin-2-one (0.700g) was added and the mixture refluxed under nitrogen for a further 2 hours. The reaction mixture was cooled and washed with water (5 × 15ml). The dried (MgSO$_4$) organic layer was evaporated to give a gum. The gum was chromatographed on silica gel eluting with ethyl acetate/petroleum ether mixtures to give 1-(1-hydroxy-1-tert-butoxycarbonylmethyl)-4-(4-phenylbut-2-ynylthio)-3-triphenylmethylamino-azetidin-2-one as a solid foam (0.490g, 55%).

$\nu_{max}$ (CHCl$_3$) 1765 cm$^{-1}$ ($\beta$-lactam); 1730 (ester).

iv. 1-(1-Hydroxy-1-t-butoxycarbonylmethyl)-4-(4-phenylbut-2-ynylthio)-3-(triphenylmethylamino)azetidin-2-one (0.100 g) was dissolved in a mixture of dry tetrahydrofuran (1ml) and dry dioxan (1ml) and the resulting solution was cooled to −5° C to −10°C. Dry pyridine (0.038g) in dry dioxan (0.5ml) was added followed by purified thionyl chloride (0.058g) in dry dioxan (0.5ml) dropwise in 3 minutes. The resulting mixture was stirred at −5°C for 1 hour. The mixture was filtered and the residue washed with dry toluene (2ml). The combined filtrates were evaporated and the residual gum extracted with dry toluene (4 × 5ml). The combined extracts were filtered and evaporated to give a gum. Re-evaporation of the gum from dry ether gave 1-(1-chloro-1-tert-butoxycarbonylmethyl)-4-(4-phenylbut-2-ynylthio)-3-triphenylmethylamino-azetidin-2-one as a solid foam (99mg, 96%).

$\nu_{max}$ (CHCl$_3$) 1775 cm$^{-1}$ ($\beta$-lactam); 1745 (ester.)

v. m-Chloroperbenzoic acid (30mg) in ethanol-free chloroform (3ml) was added in 10 minutes to a stirred solution of 1-(1-chloro-1-t-butoxycarbonylmethyl)-4-(4-phenylbut-2-ynylthio)-3-(triphenylmethylamino)azetidin-2-one (99mg) in ethanol-free chloroform (3ml) at 0°C. The mixture was stirred for a further 30 minutes at 0°C. The reaction mixture was diluted with ethanol-free chloroform (10ml) and washed successively with saturated sodium bicarbonate solution (5ml) and brine (2 × 5ml). The dried(MgSO$_4$) organic layer was evaporated to give a gum which upon re-evaporation from dry ether gave 1-(1-chloro-1-tert-butoxycarbonylmethyl)-4-(4-phenylbut-2-ynylsulphinyl)-3-triphenylmethylamino-azetidin-2-one as a solid foam (92mg, 91%)

$v_{max}$ (CHCl$_3$) 1785 cm$^{-1}$ ($\beta$-lactam); 1740 (ester).

vi. Method A

The chloro-sulphoxide from (v) above, (46mg), triphenylphosphine (37mg) and 2,6-dimethylpyridine (9mg) were stirred and heated at 50°C in a dry dioxan (1ml) under nitrogen for 12 hours. The mixture was diluted with ethyl acetate (20ml) and washed successively with N-hydrochloric acid (5ml), and brine (2 × 5ml). The dried (MgSO$_4$) organic layer was evaporated to give a gum. The gum was chromatographed on silica gel eluting with ethyl acetate/petroleum ether mixtures to give 4-(4-phenylbut-2-ynylsulphinyl)-1-(1-tert-butoxy carbonyl-1-triphenylphosphoranylidenemethyl)-3-triphenylmethylamino-azetidin-2-one as a solid (9mg, 15%)

$v_{max}$ (CHCl$_3$) 1765 cm$^{-1}$ ($\beta$-lactam); 1635 cm$^{-1}$.

Method B

The chloro-sulphoxide from (v) above (50mg), triphenylphosphine (40mg) and 1,8-bis(dimethylamino)-naphthalene (16mg) were stirred and heated at 50°C in dry dioxan (1ml) under nitrogen for 36 hours. The mixture was evaporated to give a gum which gave, after chromatography as in Method A, the desired phosphorane as a solid (7mg, 10%).

Method C

The chloro-sulphoxide from (v) above, (54mg), anhydrous lithium bromide (36mg) and triphenylphosphine (44mg) were stirred in dry tetrahydrofuran (2ml) at room temperature for 60 hours. Pyridine (2 drops) was added and the mixture was stirred for a further 10 minutes. The mixture was evaporated to give a gum which gave, after chromatography, as in Method A, the desired phosphorane as a solid (13mg, 18%).

Method D

The chloro-sulphoxide from (v) above, (1.14g), anhydrous lithium bromide (0.76g) and triphenylphosphine (0.92g) were stirred and heated at 60°C in dry tetrahydrofuran (30ml) under nitrogen for 2 hours. The mixture was cooled to room temperature and pyridine (0.14g) was added. The mixture was stirred at room temperature for 10 minutes. The work-up as in method A, gave the desired phosphorane as a solid (0.244g, 17%).

vii. 4-(4-phenylbut-2-ynylsulphinyl)-1-(1-t-butoxycarbonyl-1-triphenylphosphoranylidenemethyl)-3-(triphenylmethylamino)azetidin-2-one (244mg) was stood in piperidine (5ml) at room temperature for 24 hours. The mixture was diluted with ethyl acetate (100ml) and washed with N-hydrochloric acid (3 × 20ml) followed by brine. The dried (MgSO$_4$) organic layer was evaporated to give a gum (240mg). The gum was chromatographed on silica gel eluting with ethyl acetate/petroleum ether mixtures to give 4-(4-phenyl-2-oxobutylsulphinyl)-1-(1-tert-butoxycarbonyl-1-triphenylphosphoranylidenemethyl)-3-triphenylmethylaminoazetidin-2-one as a solid foam (204mg, 82%).

$v_{max}$ (CHCl$_3$) 1770 cm$^{-1}$ ($\beta$-lactam); 1715 cm$^{-1}$ (ester + ketone); 1635 cm$^{-1}$.

Preparation of starting materials for Example 2 i. Benzyl 6-$\beta$-(triphenylmethylamino)penicillanate (2.74g) was stirred in dry tetrahydrofuran (50ml) containing 1-bromo-3-phenylprop-2-yne (1g) under nitrogen. Sodium hydride (0.48g of 60% oil dispersion) was added and the mixture was stirred at room temperature for 48 hours. The reaction mixture was then diluted with ethyl acetate and the organic layer washed with brine and water. The dried ethyl acetate extract was evaporated to dryness and the residue triturated with ethyl acetate. Filtration gave unchanged starting material (1.05g). Chromatography of the mother liquors on silica, eluting with ethyl acetate/petroleum ether (1:9), afforded further unchanged starting ester (230mg) and 1-(1-benzyloxycarbonyl-2-methyl-1-propanyl)-3-(triphenylmethylamino)-4-(3-phenylprop-2-ynylthio)azetidin-2-one, as a foam (905mg).

$v_{max}$ (CHCl$_3$) 1760 ($\beta$-lactam, 1715 (ester), 1625 (double bond.

$\sigma$ ppm (CDCl$_3$) 2.07 (s, 3H), 2.17 (s, 3H), 2.95 (AB quartet, J=17Hz), 2.95 (b, 1H, exchanged by D$_2$O), 4.55 (broadened signal collapsing to a doublet, 1H, J=5Hz, after D$_2$O exchange), 4.93 (d, J=5Hz), 4.98 (s, 2H), 7–7.7 (m, 25H).

ii. 1-(1-Benzyloxycarbonyl-2-methyl-1-propenyl)-3-(triphenylmethylamino)-4-(3-phenylprop-2-ynylthio)azetidin-2-one (I) (3.24g) was dissolved in pyridine (30ml) and water (2ml) and the mixture was cooled in an ice-bath. Solid potassium permanganate (1.19g) was added, and the mixture stirred for one hour. Ethyl acetate and brine were added and the mixture vigorously shaken to coagulate the manganese dioxide. The latter was removed by filtering through kieselguhr, the filter cake being washed well with ethyl acetate. The organic layer was separated, washed with N-hydrochloric acid and water, dried, and evaporated to a foam (2.67g). Chromatography on silica gave unchanged starting material (826mg) and 3-(triphenylmethylamino)-4-(3-phenylprop-2-ynylthio) azetidin-2-one, as a foam (674mg). Trituration of the latter with 10% ethyl acetate /60°–80° petroleum ether gave a white solid (576mg). A sample recrystallised from ethyl acetate/60°–80° petroleum ether had m.p. 109°–110°.

$v_{max}$ (CHCl$_3$) 3300, 3230, 1765 cm$^{-1}$.

iii. 3-(Triphenylmethylamino)-4-(3-phenylprop-2-ynylthio) azetidin-2-one (526mg) and methyl glyoxylate (1.17g) were refluxed in dry benzene (25ml) with provision for the removal of water. After 1½ hours the solvent was evaporated and the residue was chromatographed on silica to give 1-(1-hydroxy-1-methoxycarbonylmethyl)-3-(triphenyl methylamino)-4-(3-phenylprop-2-ynylthio)azetidin-2-one as an amorphous solid (399 mg).

$v_{max}$ (CHCl$_3$) 3475 (—OH), 1770 ($\beta$-lactam), 1750 (ester) cm$^{-1}$.

iv. 1-(1-Hydroxy-1-methocycarbonylmethyl)-3-(triphenylmethylamino)-4-(3-phenylprop-2-ynylthio)azetidin-2-one (395mg) was dissolved in a 1:1 mixture of dry tetrahydrofuran and dioxan (14ml) and the solution, under nitrogen, was cooled to −10°. Pyridine (176mg) in dry dioxan (1ml) was then added, followed by the dropwise addition of thionyl chloride (0.153ml)

in dry dioxan (4ml) over 2–3 minutes. After a further 15 minutes the precipitated solid was filtered off and the filtrate evaporated to dryness. Dry toluene was added and was decanted from any solid. The organic solution was evaporated to give 1-(1-Chloro-1-methoxycarbonylmethyl)-3-(triphenylmethylamino)-4-(3-phenylprop-2-ynylthio)azetidin-2-one as an amorphous solid (419mg), after drying overnight in vacuo.

$v_{max}$ (CHCl$_3$) 1770 (broad, $\beta$-lactam and ester) cm$^{-1}$.

v. 1-(1-Chloro-1-methoxycarbonylmethyl)-3-(triphenylmethylamino)-4-(3-phenylprop-2-ynylthio)azetidin-2-one (419mg) was dissolved in a 1:1 mixture of dry tetrahydrofuran and dioxan (12ml) under nitrogen. Triphenylphosphine (370mg) and dry pyridine (111mg) were added and the mixture heated at 55° for 13 hours. The reaction mixture was filtered and the filtrate evaporated. The residue was taken up in dry toluene and re-evaporated. Chromatography on silica afforded 1-(-1 1-(1-methoxycarbonyl-1-triphenylphosphoranylidenemethyl)-3-(triphenylmethylamino)-4-(3-phenylprop-2-ynylthio)azetidin-2-one as a white solid (419mg).

$v_{max}$ (CHCl$_3$) 1750 (broad), 1615 (broad) cm$^{-1}$.

vi. 1-(1-Methoxycarbonyl-1-triphenylphosphoranylidenemethyl)-3-(triphenylmethylamino)-4-(3-phenylprop-2-ynylthio)azetidin-2-one (346mg) was refluxed in piperidine (8ml) containing mercuric chloride (242mg) for 8.5 hours. The mixture was stirred at room temperature for 16 hours and then filtered through celite, the filter cake being washed well with ethyl acetate and water. The organic layer was washed with dilute hydrochloric acid and brine, dried and evaporated to an amorphous solid. Chromatography on silica afforded 1-(1-methoxycabonyl-1-triphenylphosphoranylidenemethyl)-3-(triphenylmethylamino)-4-(3-phenyl-prop-2-onethio)azetidin-2-one as a white solid (245 mg).

$v_{max}$ (CHCl$_3$) 1775 (broad), 1720 (broad), 1615 (broad) cm$^{-1}$.

Preparation of starting materials for Example 3

The procedure used for the preparation of starting materials for Example 2 was followed, except that t-butyl glyoxalate was used in stage (iii) instead of methyl glyoxalate. Eventually 1-(1-t-butoxycarbonyl-1-triphenylphosphoranylidenemethyl)-3-(triphenylmethylamino)-4-(3-phenyl-2-oxopropylthio)azetidin-2-one was prepared.

$v_{max}$ (CHCl$_3$) 1755, 1720, 1635 cm$^{-1}$.

Preparation of starting materials for Example 4 i. Benzyl 6-$\beta$-(triphenylmethylamino)penicillanate (6.1g) was stirred in dry tetrahydrofuran (100ml) under nitrogen and 1-bromo-3-p-fluorophenylprop-2-yne (3.04g) was added. Potassium t-butoxide (11.1ml of a 1.1M solution in tertiary butanol, diluted with 10ml dry tetrahydrofuran) was added dropwise over 2.5 hrs. After stirring for a further 2.5 hours the mixture was diluted with ethyl acetate and the organic layer washed with brine, dried and evaporated. On trituration with ethyl acetate unchanged starting material (0.81g) was obtained as white crystals. Chromatography of the mother liquors on silica, eluting with ethyl acetate/petroleum ether (1.9) afforded further unchanged starting ester (0.525g) and 1-(1-benzyloxycarbonyl-2-methyl-1-propanyl)-3-(triphenylmethylamino)-4-(3-p-fluorophenylprop-2-ynylthio)azetidin-2-one (3.78g) which was recrystallised from ethyl acetate/petroleum ether to give white crystals m.p. 123°–4°.

$v_{max}$ (CHCl$_3$). 1758 ($\beta$-lactam), 1718 (ester), 1625 (double bond) cm$^{-1}$.

$\sigma$ ppm (CDCl$_3$). 2.02 (s, 3H); 2.17 (s, 3H); 2.94 (q, 2H, J= 16Hz, covering 1H exch. D$_2$O); 4.54 (m, 1H, collapsing to d, J=5Hz on D$_2$O exchange); 4.9 (d, 1H, J=5Hz); 4.97 (q, 2H,J=12Hz); 6.8–7.6 (24 ar).

ii. 1-(1-Benzyloxycarbonyl-2-methyl-1-propenyl)-3-(triphenylmethylamino)-4-(3-p-fluorophenylprop-2-ynylthio) azetidin-2-one (2.68g) was dissolved in pyridine (30ml) and water (2ml). The mixture was cooled in an ice bath and potassium permanganate (0.93g) added with stirring. After one hour ethyl acetate (50ml) and water (5ml) were added and sulphur dioxide was passed into the cooled mixture until it becomes colourless. The organic layer was separated, washed with saturated sodium bicarbonate solution, brine, N-hydrochloric acid and finally brine, dried and evaporated to a foam. Chromatography on silica —H gave unchanged starting material (0.77g) and 3-(triphenylmethylamino)-4-(3-p-fluorophenylprop-2-ynylthio)azetidin-2-one as a foam (0.71g).

$v_{max}$ (CHCl$_3$) 3350, 1765 cm$^{-1}$.

$\sigma$ ppm (CDCl$_3$) 2.94–3.2 (1H, exchange D$_2$O), 3.25 (s, 2H), 4.58 (2H broad peak sharpening on D$_2$O exchange), 6.22 (s, 1H exchange D$_2$O), 6.81–7.58 (Aromatic).

iii. 3-(Triphenylmethylamino)-4-(3-p-fluorophenylprop-2-ynylthio)azetidin-2-one (1.02g) and t-butyl glyoxalate (2.76g) were refluxed in dry benzene (50ml) with provision for the removal of water. After 1 hour the benzene solution was washed 5 times with water, dried and evaporated. The residue was chromatographed on silica to give 1-(1-Hydroxy-1-t-butoxycarbonylmethyl)-3-(triphenylmethylamino)-4-(3-p-fluorophenylprop-2-ynylthio)azetidin-2-one as an amorphous solid (.969g).

$v_{max}$ (CHCl$_3$) 1770, 1735 cm$^{-1}$.

iv. 1(1-Hydroxy-1-t-butoxycarbonylmethyl)-3-(triphenylmethylamino)-4-(3-p-fluorophenylprop-2-ynylthio)azetidin-2-one (570mg) was dissolved in a 1:1 mixture of dry tetrahydrofuran and dioxan (20ml) and the solution, under nitrogen, was cooled to −10°. Pyridine (224mg) in dry dioxan (5ml) was then added, followed by the dropwise addition of thionyl chloride (0.206ml) in dry dioxan (5ml) over 2–3 minutes. After a further 15 minutes the precipitated solid was filtered off and the filtrate evaporated to dryness. Dry toluene was added and was decanted from any solid. The organic solution was evaporated to dryness and re-evaporation from dry ether gave 1-(1-Chloro-1-t-butoxycarbonylmethyl)-3-(triphenylmethylamino)-4-(3-p-fluorophenylprop-2-ynylthio)azetidin-2-one as an amorphous solid.

v. 1-(1-Chloro-1-t-butoxycarbonylmethyl)-3-(triphenylmethylamino)-4-(3-p-fluorophenylprop-2-ynylthio)azetidin-2-one (570mg) was dissolved in a 1:1 mixture of dry tetrahydrofuran and dioxan (20ml) under nitrogen. Triphenylphosphine (495mg) and dry pyridine (150mg) were added and the mixture heated at 49° for 16 hours. The reaction mixture was filtered, the filtrate evaporated. The residue was triturated with toluene and the soluble portion re-evaporated. Chromatography on silica afforded 1-(1-t-butoxycarbonyl-1-triphenylphosphoranylidenemethyl)-3-(triphenylmethylamino)-4-(3-p-fluorophenylprop-2-ynylthio)azetidin-2-one, as a white solid (418mg).

$v_{max}$ (CHCl$_3$) 1745, 1630 (broad) cm$^{-1}$.

vi. 1-(1-t-Butoxycarbonyl-1-triphenylphosphoranylidenemethyl)-3-(triphenylmethylamino)-4-(3-p-fluorophenylprop-2-ynylthio)azetidin-2-one (370mg) was refluxed is piperidine (25ml) under nitrogen for 6 hours. The mixture was cooled, diluted with ethyl acetate and the organic layer washed with N-hydrochloric acid and brine, dried and evaporated to an amorphous solid. Chromatography on silica gave 1-(1-t-butoxycarbonyl-1-triphenylphosphoranylidenemethyl)-3-(triphenylmethylamino)-4-(3-p-fluorophenyl-2-oxopropylthio)azetidin-2-one as an amorphous solid (330mg).

$v_{max}$ (CHCl$_3$) 1750, 1718, 1625 (broad) cm$^{-1}$.

Preparation of starting materials for Example 5 i. Benzyl 6-β-(triphenylmethylamino)penicillanate (1.1g) in dry tetrahydrofuran (40ml) containing 1-bromobut-2-yne (0.3g) (under N$_2$) was treated with sodium hydride (0.2g of 50% dispersion) and refluxed for 7 hours and then left stirring overnight at room temperature. The reaction mixture was diluted with ethyl acetate (150ml) and washed with brine and water. The dried ethyl acetate extract was evaporated to dryness and the residue triturated with ethyl acetate. Filtration gave unchanged (I) (0.5g). Chromatography of the mother liquors on silica, eluting with ethyl acetate light petroleum (3:7) gave more unchanged starting material (0.11g) and then 1-(1-benzyloxycarbonyl-2-methyl-1-propenyl)-3-(triphenylmethylamino)-4-(but-2-ynylthio)azetidin-2-one as a foam (0.25g).

$v_{max}$ (CHCl$_3$) 1760 cm$^{-1}$ (β-lactam carbonyl), 1720 cm$^{-1}$ (ester), 1625 cm$^{-1}$ (C = C)

ν ppm (CDCl$_3$) 1.67 (t, 3H, J=2.5Hz); 2.00 (s, 3H); 2.22 (s, 3H); 2.63 (q, 2H, J=2.5Hz); 2.92 (d, 1H, exch. NH); 4.50 (dd, 1H, collapsing to singlet J=5H D$_2$O exchange 4.75 (d, 1H, J=5Hz); 5.08 (q, 2H, J=12Hz); 7.1–7.6 (Ar, 20H).

ii. 1-(1-Benzyloxycarbonyl-2-methyl-1-propenyl)-3-(triphenylmethylamino)-4-(but-2-ynylthio)azetidin-2-one (4.4g) was dissolved in dimethylformamide (40ml), water (4ml) and pyridine (1.6ml) and the mixture cooled to −20°. Solid potassium permanganate (1.74g) was added, and the mixture stirred between −20° and −5° for two hours. Ether and water were then added and the mixture shaken. After filtering through Keiselguhr, the organic layer was washed with N hydrochloric acid and brine, dried and evaporated to give an amorphous solid (2.73g). Chromatography on silica —H gave unchanged starting material (0.7g) and 3-(triphenylmethylamino)-4-(but-2-ynylthio)azetidin-2-one (1.2g) as a foam.

$v_{max}$ (CHCl$_3$) 3370, 1770 cm$^{-1}$.

σ ppm (CDCl$_3$) 1.73 (t, 3H, J=3Hz), 2.97 (q, 2H, J=3Hz), 4.50 (broadened signal 2H, collapsing to sharp singlet on D$_2$O exchange), 6.54 (b.s., 1H, exchange), 7.1–7.7 (Ar, 15H).

iii. 3-(Triphenylmethylamino)-4-(but-2-ynylthio)azetidin-2-one (1.03g) and t-butyl glyoxalate (3.3g) were refluxed in dry benzene (50ml) with provision for the removal of water. After one hour the benzene solution was washed 5 times with water, dried and evaporated. Chromatography of the residue on silica —H gave 1-(1-hydroxy-1-t-butoxycarbonylmethyl)-3-(triphenylmethylamino)-4-(but-2-ynylthio)azetidin-2-one as an amorphous white solid (0.978 g).

$v_{max}$ (CHCl$_3$) 3400, 1765, 1730 cm$^{-1}$.

iv. 1-(1-Hydroxy-1-t-butoxycarbonylmethyl)-3-(triphenylmethylamino)-4-(but-2-ynylthio)azetidin-2-one (0.44g) was dissolved in a 1:1 mixture of dry tetrahydrofuran and dioxan (10ml) and the solution, under nitrogen, was cooled to −10°. Pyridine (0.2g) in dry dioxan (2.5ml) was added, followed by the dropwise addition of thionyl chloride (0.19ml) in dioxan (2.5ml) over 2–3 minutes. After a further 15 minutes the precipitated solid was filtered off and the filtrate evaporated to dryness. Dry toluene was added to the residue and decanted off from any solid. The organic solution was evaporated to dryness and re-evaporation from dry ether gave 1-(1-chloro-1-t-butoxycarbonylmethyl)-3-(triphenylmethylamino)-4-(but-2-ynylthio)azetidin-2-one as an amorphous solid (0.45g).

$v_{max}$ (CHCl$_3$) 1775, 1740 cm$^{-1}$.

This chloride, without further purification was dissolved in ethanol-free chloroform and the solution, under nitrogen, was cooled in an ice-bath. m-chloroperbenzoic acid (0.16g) in chloroform was added dropwise over a few minutes. After a further 30 minutes the organic solution was washed with saturated aqueous sodium bicarbonate, then with brine, and finally dried and evaporated. Re-evaporation of the residue from dry ether gave 1-(1-chloro-1-t-butoxycarbonylmethyl)-3-(triphenylmethylamino)-4-(but-2-ynylthio)azetidin-2-one sulphoxide as an amorphous solid.

$v_{max}$ (CHCl$_3$) 1785, 1740 cm$^{-1}$.

This sulphodixe, without further purification, was treated under nitrogen with triphenylphosphine (0.52g) and 2,6-dimethyl pyridine (0.125g) in dry dioxan (10ml) at 50° for 17 hours. The mixture was filtered and the filtrate evaporated to dryness. Chromatography on silica —H gave 1-(1-t-butoxycarbonyl-1-triphenylphosphoranylidenemethyl)-3-(triphenylmethylamino)-4-(but-2-ynylthio)azetidin-2-one sulphoxide (0.2g) as a white solid.

$v_{max}$ (CHCl$_3$) 1760 (b), 1730 (b) cm$^{-1}$.

v. 1-(1-t-Butoxycarbonyl-1-triphenylphosphoranylidenemethyl)-3-(triphenylmethylamino)-4-(but-2-ynylthio)azetidin-2-one sulphoxide (0.39g) was treated with piperidine (40ml) at room tempertaure for 24 hours. Ethyl acetate was added and the organic phase washed with N-hydrochloric acid (x 3) and brine, dried and evaporated. Chromatography on silica —H gave 1-(1-t-butoxycarbonyl-1-triphenylphosphoranylidenemethyl)-3-(triphenylmethylamino)-4-(2-oxobutylthio)azetidin-2-one sulphoxide (0.27g), obtained as a white solid.

$v_{max}$ (CHCl$_3$) 1765, 1710, 1635 (b) cm$^{-1}$.

Preparation of starting materials for Example 6 i. Benzyl 6-β-(triphenylmethylamino)penicillanate (7.17g) was stirred in dry tetrahydrofuran (90ml) containing 1-bromo-4-tetrahydropyranyloxy-but-2-yne(3.1g) under nitrogen, and a solution of potassium t-butoxide (1.4g) in t-butanol (12.5ml) in dry tetrahydrofuran (10ml) was added dropwise over 30 minutes. After stirring for a further 1 hour the reaction mixture was worked-up as before. The crude product was chromatographed on silica (100g) eluting with ethyl acetate/petroleum ether (1:9) to give 1-(1-benzyloxycarbonyl-2-methyl-1-propenyl)-3-(triphenylmethylamino)-4-(4-tetrahydropyranyloxybut-8c 2-ynylthio)azetidin-2-one as an amorphous solid (4.05g).

$v_{max}$ (CHCl$_3$) 1755 ($\beta$-lactam), 1715 (ester) 1620 (double bond) cm$^{-1}$.

$\sigma$ ppm (CDCl$_3$) 1.6 (m, 6H), 1.98 (s, 3H), 2.21 (s, 3H), 2.72 (2H, AB quartet J=15Hz each signal being further split with J=1.5Hz), 2.9 (m, 1H, D$_2$O exchanged), 3.55 (m, 1H), 4.98 (t, 2H, J=1.5Hz), 4.5 (m, 1H, collapsing to doublet J=5Hz on D$_2$O exchange), 4.75 (d, 1H, J=5Hz), 5.07 (q, 2H, J=12Hz), 7.1–7.6 (m, 20H).

ii. 1-(1-Benzyloxycarbonyl-2-methyl-1-propenyl)-3-(triphenylmethylamino)-4-(4-tetrahydropyranyloxybut-2-ynylthio)azetidin-2-one (7g) in dimethylformamide (50ml) containing water (5ml) and pyridine (2ml) was cooled to −10° and powdered potassium permanganate (2.4g) was added all at once. After 1 hour at −10° the mixture was poured into ether, shaken with brine and filtered through kieselguhr. The ether layer was separated, washed with a little dilute hydrochloric acid followed by brine, dried, and evaporated. Chromatography on silica afforded unchanged starting material (2.03g) and the required product 3-(triphenylmethylamino)-4-(4-tetrahydropyranyloxybut-2-ynylthio)azetidin-2-one (1.36g) as an amorphous solid.

$v_{max}$ (CHCl$_3$) 3400, 3300, 1768 cm$^{-1}$.

$\sigma$ ppm (CDCl$_3$) 1.63 (broad singlet, 6H), 3.17 (t, 2H, J=2Hz), 3.00 (m, 1H, D$_2$O exchanged), 3.7 (m, 3H), 4.23 (t, 2H, J=2Hz), 4.63 (m, 2H), 6.7 (broad singlet, 1H, D$_2$O exchanged), 7.0–7.6 (m, 15H).

ii. 3-Triphenylmethylamino)-4-(4-tetrahydropyranyloxybut-2-ynylthio)azetidin-2-one (934mg) and t-butylglyoxylate (2.5g) were refluxed in benzene (20ml) with provision for the removal of water. After 1 hour the cooled solution was washed with water (6 × 5ml), dried and evaporated. Chromatography on silica gave 1-(1-hydroxy-1-t-butoxycarbonylmethyl)-3-(triphenylmethylamino)-4-(4-tetrahydropyranyloxybut-2-ynylthio)azetidine-2-one which still contained some t-butylglyoxylate. Re-chromatography on silica afforded the pure material as an amorphous solid (519mg)

$v_{max}$ (CHCl$_3$) 3500, 3350, 1770, 1738 cm$^{-1}$.

(iv) 1-(1-Hydroxy-1-t-butoxycarbonylmethyl)-3-(triphenylmethylamino)-4-(4-tetrahydropyranyloxybut-2-ynylthio) azetidin-2-one (646mg) was dissolved in dry THF/dioxan (1:1, 12ml) and the solution, under nitrogen, was cooled to −15°. Dry pyridine (227mg) in dioxan (1ml) was then added followed by the dropwise addition of thionyl chloride (357mg) in 1:1 tetrahydrofuran/dioxan (5ml) over 1–2 minutes. After a further 15 minutes the precipitated solid was filtered off and the filtrate evaporated to dryness. Dry toluene was added and the solution decanted from any solid, and evaporated to give 1-(1-chloro-1-t-butoxycarbonylmethyl)-3-(triphenylmethylamino)-4-(4-tetrahydropyranyloxybut-2-ynylthio)azetidine-2-one as an amorphous solid (650mg) after drying overnight in vacuo.

$v_{max}$ (CHCl$_3$) 1780, 1745 cm$^{-1}$.

v. 1-(1-chloro-1-t-butoxycarbonylmethyl)-3-(triphenylmethylamino)-4-(4-tetrahydropyranyloxybut-2-ynylthio) azetidin-2-one (650mg) was dissolved in 1:1 THF/dioxan (12ml) under nitrogen. Triphenylphosphine (525mg) and pyridine (158mg) were added and the mixture heated at 55° for 15.5 hours. The reaction mixture was filtered and the filtrate evaporated. Dry toluene was added to the residue and the solution decanted from any solid and evaporated. Chromatography on silica afforded 1-(1-t-butoxycarbonyl-1-triphenylphosphoranylidenemethyl)-3-(triphenylmethylamino)-4-(4-tetrahydropyranyloxybut-2-ynylthio)azetidin-2-one as an amorphous solid (470mg).

$v_{max}$ (CHCl$_3$) 1755, 1638 cm$^{-1}$.

vi. 1-(1-t-Butoxycarbonyl-1-triphenylphosphoranylidenemethyl)-3-(triphenylmethylamino)-4-(4-tetrahydropyranyloxybut-2-ynylthio)azetidin-2-one (462mg) in piperidine (7ml) was refluxed under nitrogen for 17½ hours. The solvent was removed under reduced pressure and the residue taken up in ethyl acetate. The solution was washed with a little dilute hydrochloric acid followed by brine, dried and evaporated. Chromatography on silica afforded unchanged starting material (47mg) 1-(1-t-butoxycarbonyl-1-triphenylposphoranylidenemethyl)-3-(triphenylmethylamino)-4-(4-tetrahydropyranyloxy-2-oxobutylthio)azetidin-2-one as an amorphous solid (224 mg).

$v_{max}$ (CHCl$_3$) 1778, 1720, 1638 cm$^{-1}$.

Preparation of starting material for Example 7 i. Benzyl 6-triphenylmethylamino-penicillanate (30g) was suspended in dry tetrahydrofuran (500ml) under nitrogen and 1-bromo-3-(2-tetrahydropyranyl)-prop-2-yne (11.7g) was added. A 0.78M solution of potassium t-butoxide in t-butanol (78ml) was then added dropwise under nitrogen to the stirred mixture over 3 hours. The mixture was stirred under nitrogen for 1 hour after the complete addition of the butoxide, then ethyl acetate was added and the solution was washed with brine followed by water. The organic layer was dried (MgSO$_4$) and evaporated to leave an oil which was chromatographed on silica, eluting with petroleum (b.p. 60°–80°)/ethyl acetate in 9:1, 17:3 and 8:2 mixtures. The product 1-(1-benzyloxycarbonyl-2-methyl-1-propenyl)-3-triphenylmethylamino-1-[3-(2-tetrahydropyranyl)-propynylthio]azetidin-2-one was obtained as a foam (19g).

$v_{max}$(CHCl$_3$), 1755 cm$^{-1}$ ($\beta$-lactam carbonyl), 1718 cm$^{-1}$ (ester), 1625 cm$^{-1}$ (C=C).

$\sigma$ ppm (CDCl$_3$) 1.1–1.9 (broad s, 6H); 1.99 (s, 3H); 3.3–5.0 (complex, 5H); AB q. centred at 5.1 (2H), 7.1–7.2 (m, 20H).

ii. 1-(1-Benzyloxycarbonyl-2-methyl-1-propenyl)-3-(triphenylmethylamino)-4-[3-(2-tetrahydropyranyl)-prop-2-ynylthio)]azetidin-2-one (2.2g) was dissolved in pyridine (20ml) amd water (2ml) was added. The mixture was stirred and cooled in an ice-salt bath and finely ground potassium permanganate (780mg) was added. The mixture was stirred with cooling for 1 hour and then ethyl acetate/brine was added. Sulphur dioxide was passed into the mixture until all the manganese dioxide had dissolved, and then the layers were separated and the organic layer was washed successively with aqueous sodium bicarbonate, N.HCl, and brine. The dried (MgSO$_4$) organic layer was evaporated to an oil and chromatographed on silica gel, eluting with ethyl acetate/petroleum (b.p. 60°–80°) in 2:8 and 3:7 mixtures, to give 4[3-(2-tetrahydropyranyl)prop-2-ynylthio]-3-triphenylmethylamino-azetidin-2-one (340mg) in later fractions.

$v_{max}$ (CHCl$_3$) 1765 cm$^{-1}$.

iii. Tert-butylglyoxylate hydrate (370mg) was refluxed in dry benzene (8ml) with provision for the removal of water present and then 4[3-(2-tetrahydropyranyl)prop-2-ynylthio]-3-(triphenylmethylamino)azetidin-2-one (120mg) was added in benzene (4ml) and the mixture refluxed. After 2¾ hours the mixture was cooled and benzene was added. The benzene solution was washed five times with water and once with brine, dried (MgSO₄) and evaporated to an oil which was chromatographed on silica gel, eluting with ethyl acetate/petroleum (b.p. 60°–80°) in 2:8 and 7:3 mixtures. This led to the isolation of 1-(1-hydroxy-1-tert-butoxycarbonylmethyl)-3-(triphenyl-methylamino)-4-[3-(2-tetrahydropyranyl)prop-2-ynyl-thio]-azetidin-2-one (90mg)

$v_{max}$ (CHCl₃) 1775 cm⁻¹ (b-lactam C=O) and 1740 cm⁻¹ (ester C=O).

iv. 1-(1-Hydroxy-1-t-butoxycarbonylmethyl)-3-(triphenylmethylamino)-4-[3-(2-tetrahydropyranyl)prop-2-ynylthio] azetidin-2-one (2.7g) was taken up in tetrahydrofuran (50ml) and the solution was cooled to −15° and then pyridine (0.5ml) in tetrahydrofuran (15ml) were added to the cooled solution. The mixture was stirred at −15° for 45 minutes and then at room temperature for 15 minutes. Toluene was then added and the precipitated pyridinium hydrochloride was filtered off. The solvent in the filtrate was removed to leave crude 1-(1-t-butoxycarbonyl-1-chloromethyl)-3-(triphenyl-methylamino) -4-[3-(2-tetrahydropyranyl)-prop-2-ynylthio]azetidin-2-one as an oil.

$v_{max}$ (CHCl₃) 1775 cm⁻¹ (β-lactum C=O) and 1745 cm⁻¹ (ester C=O).

Tetrahydrofuran (30ml) and dioxan (25ml) were added to the crude chloride, the solution was warmed to 50°, and then triphenylphosphine (1.45g) and pyridine (0.5ml) were added. After stirring at 55° for 21 hours, the solvents were removed and the crude product was chromatographed on silica gel, eluting with petroleum (b.p. 60°–80°)/ethyl acetate (7:3). This gave 1-(1-tert-butoxycarbonyl-1-triphenylphos-phoranylidenemethyl)-3-(triphenylmethylamino)-1-[3-(2-tetrahydropyranyl)-prop-2-ynylthio]azetidin-2-one as a glass (1.96g), $v_{max}$ (CHCl₃) 1750 cm⁻¹, 1635 cm⁻¹.

v. 1-(1-t-Butoxycarbonyl-1-triphenylphos-phoranyledenemethyl)-3-(triphenylmethylamino)-4-[3-(2-tetrahydropyranyl)-prop-2-ynylthio]azetidin-2-one, (1.86g) was taken up in pyrrolidine (15ml) and the mixture was refluxed under nitrogen for 19 hours. The pyrrolidine was then removed and the residue taken up in chloroform (150ml) and washed with 0.5N HCl (1 × 100ml, 2 × 50ml), followed by brine. The chloroform solution was then dried (MgSO₄) and evaporated to an oil, which was chromatographed on silica gel (20g), using a gradient elution of petroleum (b.p. 60°–80°)/ethyl acetate (from 7:3 to 1:1). This led to the isolation of 1(1-tert-butoxycarbonyl-1-triphenylphos-phoranylidenemethyl)-3-(triphenylmethylamino)-4-[3-(2-tetrahydropyranyl)-prop-2-onethio]azetidin-2-one (700mg)

$v_{max}$ (CHCl₃) 1755; 1710, and 1635 cm⁻¹.

We claim:

1. A compound of the formula:

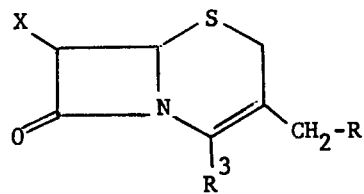

wherein X is 2-thienylacetamido; R³ is a carboxylic acid group or a non-toxic salt thereof; and R is 2'-tetrahydropyranyl.

2. The compound of claim 1 which is 3-(2'-tetrahydropyranylmethyl)-7-(2-thienylacetamido)-3-cephem-4-carboxylic acid.

* * * * *